(12) United States Patent
Walulik et al.

(10) Patent No.: US 6,616,664 B2
(45) Date of Patent: Sep. 9, 2003

(54) CLAMP ASSEMBLY FOR AN EXTERNAL FIXATION SYSTEM

(75) Inventors: Stephen B. Walulik, Phillipsburg, NJ (US); Kirk J. Bailey, Blairstown, NJ (US)

(73) Assignee: EBI L.P., Parsippany, NJ (US)

( * ) Notice: Subject to any disclaimer, the term of this patent is extended or adjusted under 35 U.S.C. 154(b) by 0 days.

(21) Appl. No.: 09/918,138

(22) Filed: Jul. 30, 2001

(65) Prior Publication Data

US 2002/0026190 A1 Feb. 28, 2002

Related U.S. Application Data

(63) Continuation-in-part of application No. 09/422,377, filed on Oct. 21, 1999, now Pat. No. 6,277,119.

(51) Int. Cl.$^7$ .............................................. A61B 17/60
(52) U.S. Cl. ............................. 606/57; 604/54; 604/55; 604/56; 604/58; 604/59; 604/61; 600/230; 600/234
(58) Field of Search ...................... 606/54–61; 600/234, 600/230; 269/37

(56) References Cited

U.S. PATENT DOCUMENTS

| | | | | |
|---|---|---|---|---|
| 4,488,542 A | | 12/1984 | Helland ..................... 128/92 A |
| 4,553,273 A | | 11/1985 | Wu ............................. 623/18 |
| 4,600,000 A | | 7/1986 | Edwards ..................... 128/92 |
| 4,620,533 A | | 11/1986 | Mears ...................... 128/92 Z |
| 4,657,550 A | | 4/1987 | Daher ......................... 623/17 |
| 4,662,365 A | | 5/1987 | Gotzen et al. ................ 128/92 |
| 4,718,151 A | * | 1/1988 | LeVahn et al. ............... 24/535 |
| 4,867,404 A | * | 9/1989 | Harrington et al. ........... 24/523 |
| 5,020,195 A | * | 6/1991 | LeVahn ....................... 24/514 |
| 5,025,780 A | * | 6/1991 | Farley ......................... 403/18 |
| 5,211,664 A | | 5/1993 | Tepic et al. .................. 623/16 |
| 5,242,240 A | * | 9/1993 | Gorham ...................... 403/389 |
| 5,261,912 A | | 11/1993 | Frigg .......................... 606/61 |
| 5,352,224 A | | 10/1994 | Westermann ................ 606/61 |
| 5,393,161 A | | 2/1995 | Mata et al. ................. 403/133 |
| 5,403,315 A | | 4/1995 | Ashman ...................... 606/61 |
| 5,451,225 A | | 9/1995 | Ross, Jr. et al. .............. 606/59 |
| 5,520,689 A | | 5/1996 | Schlapfer et al. ............. 606/61 |
| 5,527,311 A | | 6/1996 | Procter et al. ................ 606/61 |
| 5,534,002 A | | 7/1996 | Brumfield et al. ............ 606/61 |
| 5,542,946 A | | 8/1996 | Logroscino et al. .......... 606/61 |
| 5,562,662 A | | 10/1996 | Brumfield et al. ............ 606/61 |
| 5,601,552 A | | 2/1997 | Cotrel ......................... 606/61 |

(List continued on next page.)

FOREIGN PATENT DOCUMENTS

WO    WO 98/32385    7/1998

OTHER PUBLICATIONS

Howmedica, Inc. manual entitled "External Fixation of a Complex Femoral Fracture, Frame Construction Manual", copyright 1981, 24 pages.
Howmedica brochure entitled "Howmedica Trauma Simple Solutions", copyright 1998, 26 pages.
Synthes brochure entitled "The AO/ASIF Hybrid Fixator Technique Guide", copyright 1995, 25 pages.

Primary Examiner—Gregory L. Huson
Assistant Examiner—Azadeh Kokabi
(74) Attorney, Agent, or Firm—Harness, Dickey & Pierce, P.L.C.

(57) ABSTRACT

A clamp assembly for an external fixation system includes a first clamp member receiving a first elongated and a second clamp member receiving a second elongated member. The first clamp member includes a first fastener rotatably in a first direction to lock the first elongated member relative to the first clamp member. A second fastener connects the first and second clamp members. The second fastener is rotatable in the first direction to independently lock the second elongated member relative to the second clamp member. The first fastener is hollow and the second fastener passes through the first fastener.

29 Claims, 18 Drawing Sheets

U.S. PATENT DOCUMENTS

| | | |
|---|---|---|
| 5,624,440 A | 4/1997 | Huebner ................. 606/59 |
| 5,643,258 A | 7/1997 | Robioneck et al. ........... 606/54 |
| 5,676,666 A | 10/1997 | Oxland et al. ............. 606/61 |
| 5,683,389 A | 11/1997 | Orsak ................... 606/59 |
| 5,683,390 A | 11/1997 | Metz-Stavenhagen et al. ................. 606/61 |
| 5,688,272 A | 11/1997 | Montague et al. ............ 606/61 |
| 5,688,274 A | 11/1997 | Errico et al. ................. 606/61 |
| 5,702,393 A | 12/1997 | Pfaifer ................... 606/61 |
| 5,709,681 A | 1/1998 | Pennig ................... 606/54 |
| 5,741,252 A | 4/1998 | Mazzio et al. ............. 606/54 |
| 5,741,254 A | 4/1998 | Henry et al. ................. 606/61 |
| 5,743,911 A | 4/1998 | Cotrel ................... 606/61 |
| 5,746,741 A | 5/1998 | Kraus et al. ................. 606/54 |
| 5,752,954 A | 5/1998 | Mata et al. ................. 606/59 |
| 5,776,134 A * | 7/1998 | Howland ................. 606/61 |
| 5,782,833 A * | 7/1998 | Haider ................... 606/61 |
| 5,863,292 A * | 1/1999 | Tosic ................... 606/56 |
| 5,863,293 A | 1/1999 | Richelsoph ............... 606/61 |
| 5,888,221 A | 3/1999 | Gelbard ................. 623/17 |
| 5,891,144 A | 4/1999 | Mata et al. ................. 606/59 |
| 5,921,985 A | 7/1999 | Ross, Jr. et al. ............. 606/59 |
| 5,928,230 A | 7/1999 | Tosic ................... 606/57 |
| 5,961,515 A | 10/1999 | Taylor et al. ............. 606/59 |
| 6,017,306 A * | 1/2000 | Bigliani et al. ............. 600/227 |
| 6,077,263 A * | 6/2000 | Ameil et al. ............. 606/61 |
| 6,083,154 A * | 7/2000 | Liu et al. ................. 600/231 |
| 6,110,173 A * | 8/2000 | Thomas, Jr. ............. 606/61 |

* cited by examiner

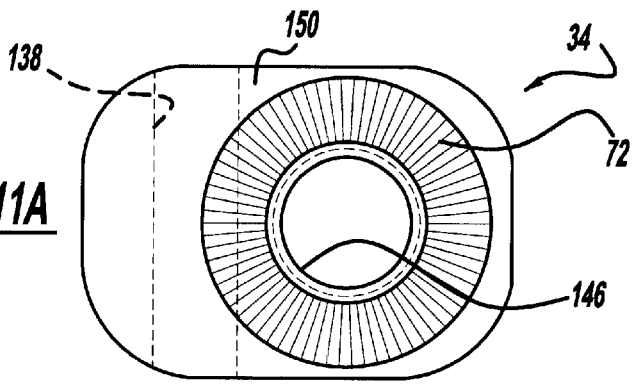
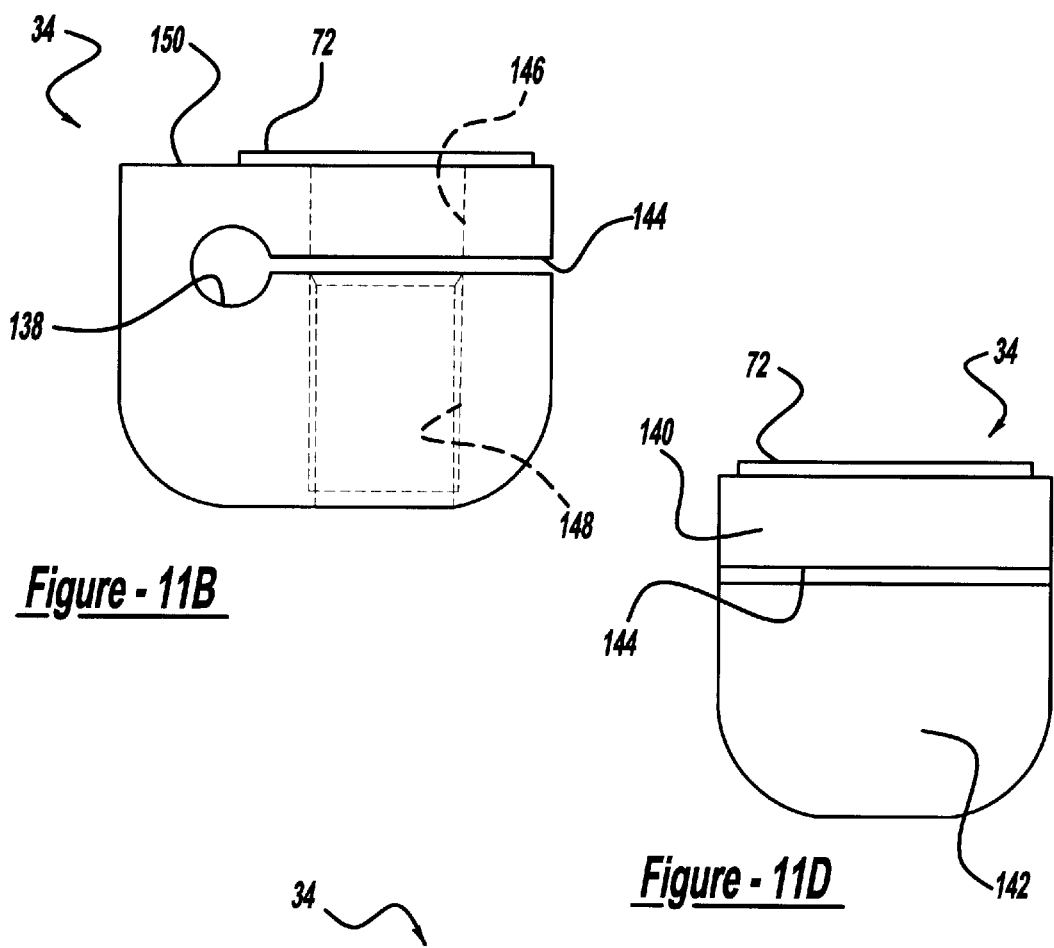
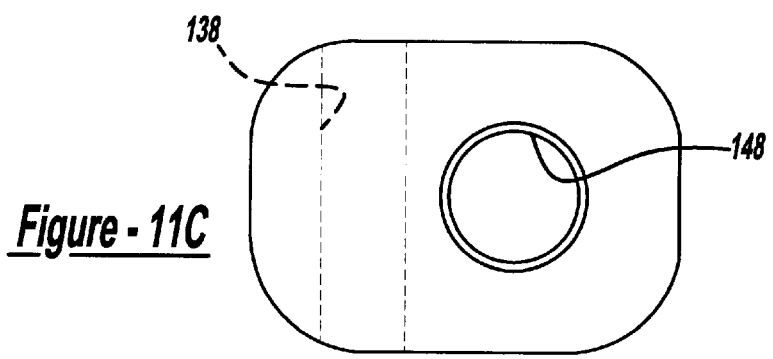
*Figure - 11A*
*Figure - 11B*
*Figure - 11C*
*Figure - 11D*

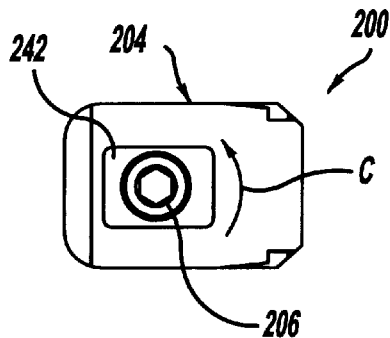
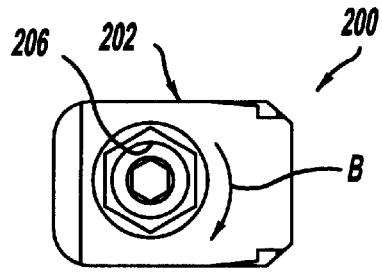
*Figure - 20*
*Figure - 21*
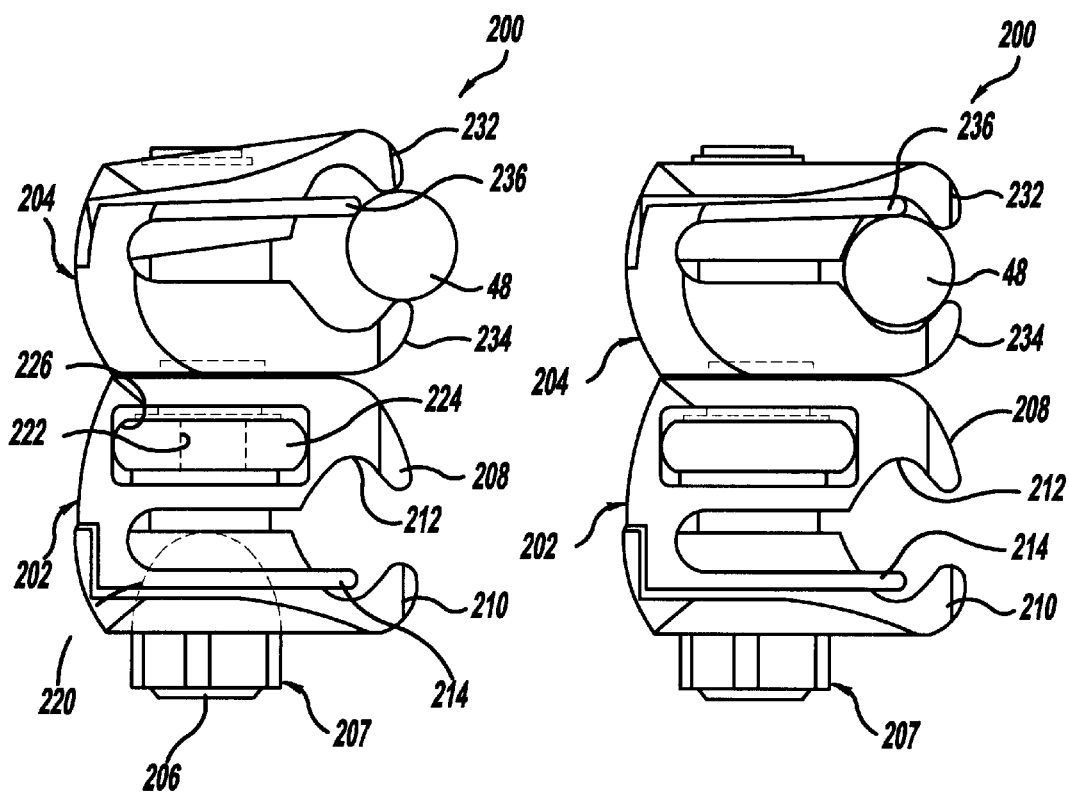
*Figure - 22*
*Figure - 23*

CLAMP ASSEMBLY FOR AN EXTERNAL FIXATION SYSTEM

CROSS-REFERENCE TO RELATED APPLICATION

This is a continuation-in-part of an application filed on Oct. 21, 1999 and assigned U.S. Ser. No. 09/422,377 now U.S. Pat. No. 6,277,119.

FIELD OF THE INVENTION

The present invention relates generally to an external fixation system for bones. More particularly, the present invention relates to a clamp assembly for securing two bars of an external fixation.

BACKGROUND OF THE INVENTION

In various orthopedic surgical procedures, it is often necessary to secure two or more portions of bone in a relatively fixed relationship to each other. This need is often the result of a fracture which has occurred to the bone. To ensure that the bone can properly regenerate and fuse the fractures of the bone, it is important that the various bone portions be fixed at the desired position during bone regeneration.

Various external fixation devices for the repair of traumatized bone are known. For example, commonly assigned U.S. Pat. No. 5,620,442 to Bailey et al. discloses an apparatus for the external fixation of small bones. The apparatus is illustrated to include a bone screw clamp for receiving a first bone screw which is connected to a first bone portion. The external fixator further includes a bone screw clamp which is operable to receive a second bone screw connected to the second bone portion. The first and second bone screw clamps include a spherical portion. The external fixator further includes a connection member for securing the spherical portions of the bone screw clamps. The connection member defines a radiographic window to permit radiographic examination of the bone fracture without removing the apparatus. U.S. Pat. No. 5,620,442 is hereby incorporated by reference as if fully set forth herein.

While known fixators, including the type described above, have proven to be effective for the fixation of bones, they nevertheless can be the subject of certain improvements. In this regard, conventional external fixation devices often do not provide the flexibility required for particular applications. Thus, it would be advantageous to provide an external fixation system with a plurality of interchangeable and distinct components which allow for a greater degree of surgeon flexibility in producing a desired construction.

SUMMARY OF THE INVENTION

According to one aspect, the present invention relates to an external fixation system operable for securing two portions of bone in a fixed relationship to each other including various interchangeable components which can be selected by a surgeon.

According to another aspect, the present invention relates to a clamp assembly for securing two cylindrical members of an external fixation system.

An advantage of the present invention is to provide an external fixation system for bones and a related method that permit independent placement of bone pins at various positions and angular orientations along a bone.

Another advantage of the present invention is to provide an external fixation system for bones and a related method that incorporate a universal base clamp which can be placed any free space along a support rod without requiring the removal of other elements that may be secured to the support rod.

Another advantage of the present invention is to provide an external fixation system for bones and a related method that include a compression/distraction arrangement for relatively translating a pair of spaced apart support rods.

Another advantage of the present invention is to provide an external fixation system for bones and a related method that include a telescoping bone screw clamp that allows a surgeon to displace a bone pin from a support rod.

Another advantage of the present invention is to provide an external fixation system for bones and a related method that include a plurality of distinct components including cooperating serrated portions for facilitating interconnection between the components.

A related advantage of the present invention is to provide an external fixation system for bones and a related method that include a plurality of distinct components each including one of a cylindrical rod and a rod receiving portion to facilitate interconnection between the components and a cylindrical support rod.

Another advantage of the present invention is to provide a clamp assembly for an external fixation system operable for adjustably securing two cylindrical rods.

Another advantage of the present invention is to provide a clamp assembly for an external fixation system that may be secured to a cylindrical rod anywhere along the length of the cylindrical rod.

Another advantage of the present invention is to provide a clamp assembly for an external fixation system that may be fixedly secured to a first cylindrical rod while it is being adjusted relative to a second cylindrical rod.

Another advantage of the present invention is to provide a clamp assembly for an external fixation system in which a relative angular orientation between first and second cylindrical rods can be locked while one of the cylindrical rods is translated along its axis such that associated bone segments can be lengthened.

It is a related object of the present invention to provide a clamp assembly for an external fixation system which can be rigidly locked to a first cylindrical rod and adjusted relative to a second cylindrical rod such that the first cylindrical rod is used as a reference while associated bone segments are manipulated.

Additional advantages and features of the present invention will become apparent from the following description and appended claims, taken in conjunction with the accompanying drawings.

BRIEF DESCRIPTION OF THE DRAWINGS

The present invention will become more fully understood from the detailed description and the accompanying drawings, wherein:

FIGS. 11A through 11D are views of a bone pin clamp body of the external fixation system according to the teachings of the preferred embodiment of the present invention.

FIG. 20 is a top view of the clamp assembly according to the teachings of the preferred embodiment of the present invention.

FIG. 21 is a bottom view of the clamp assembly according to the teachings of the preferred embodiment of the present invention.

FIG. 22 is a side view similar to FIG. 19 illustrating a cylindrical rod being introduced into an upper clamp member of the clamp assembly.

FIG. 23 is another view similar to FIG. 19 illustrating a cylindrical rod fully seated within the upper clamp member.

DETAILED DESCRIPTION OF THE PREFERRED EMBODIMENTS

The following description of the preferred embodiment of the present invention is merely exemplary in nature and is in no way intended to limit the invention or its application or uses.

Figure 1A:
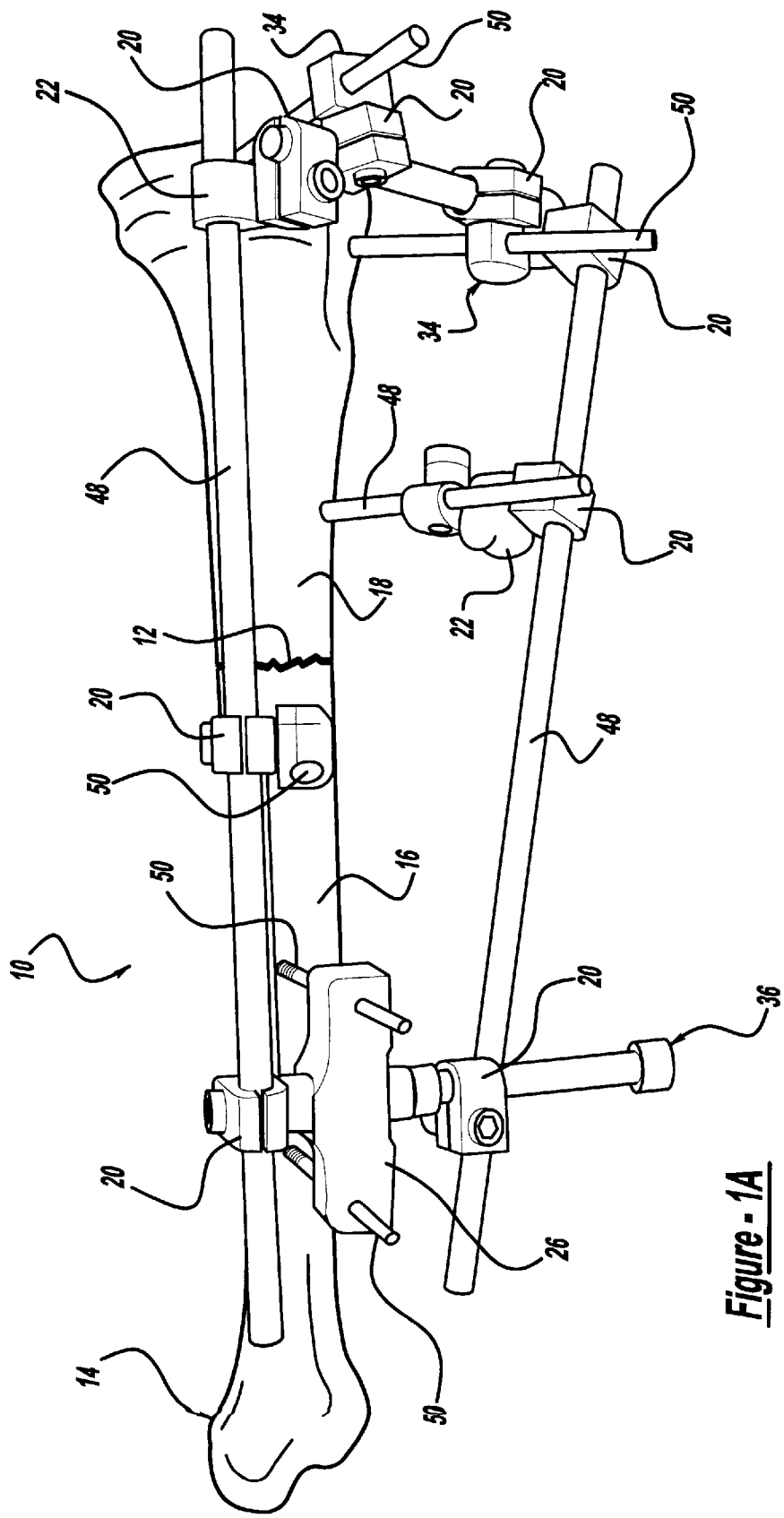
FIGS. 1A and 1B illustrate a first exemplary construct of components of the external fixation system according to the teachings of the preferred embodiment of the present invention in operative association with a tibia.
Figure 1B:
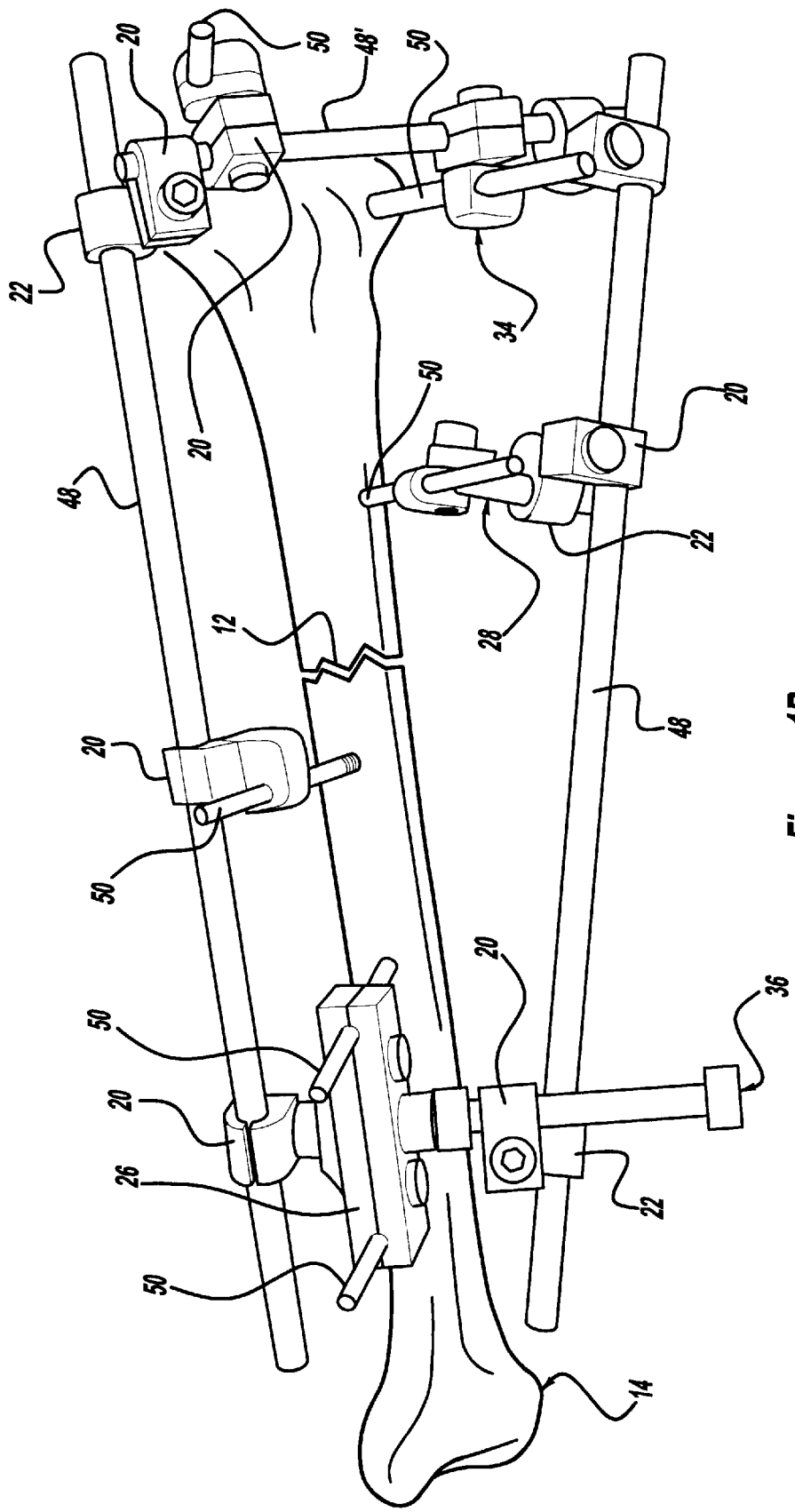
Figure 2:
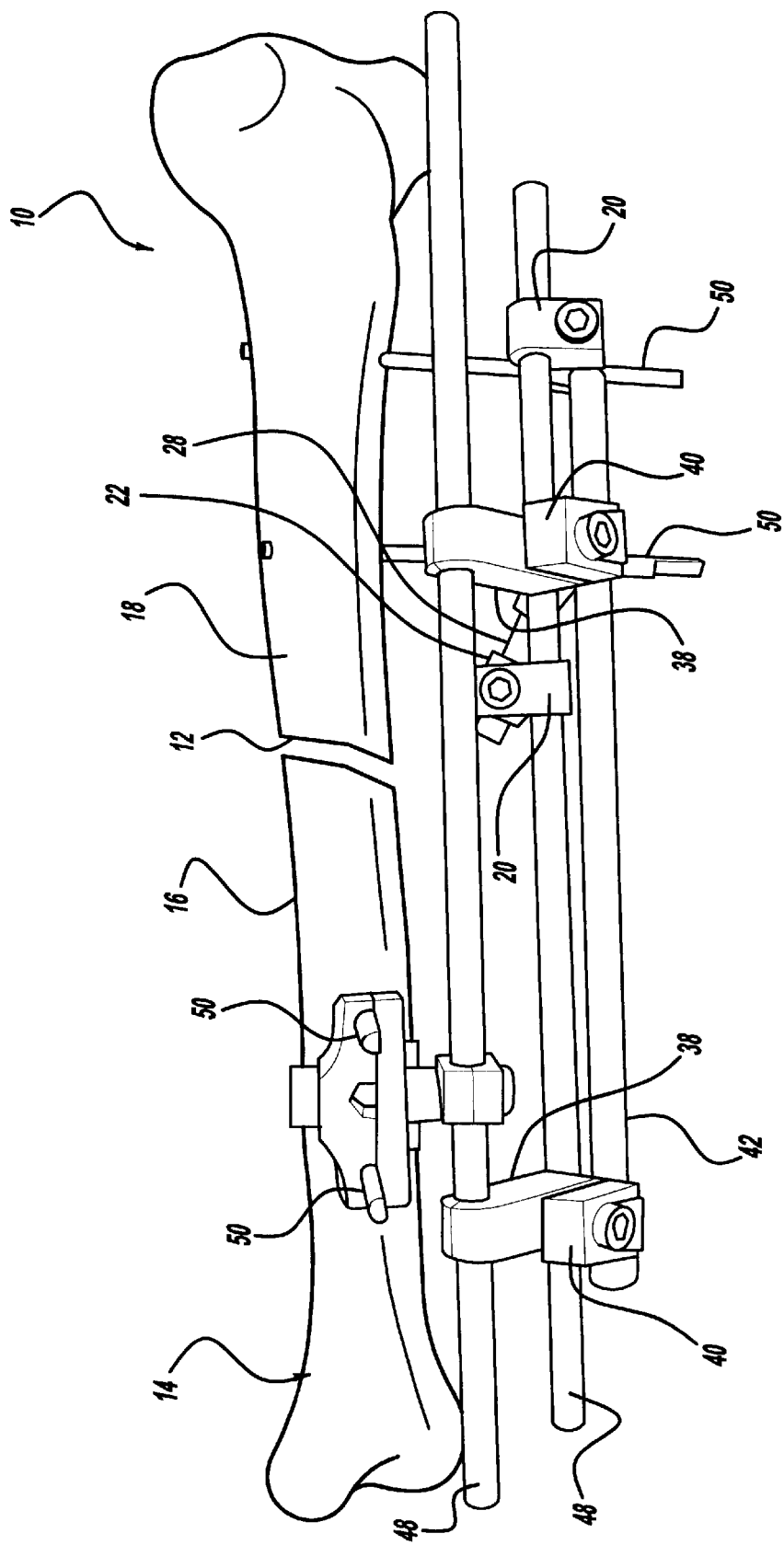
FIG. 2 illustrates a second exemplary construct of components of the external fixation system according to the teachings of the preferred embodiment of the present invention in operative association with a tibia, the second construct incorporating a compression/distraction arrangement.

Referring initially to FIGS. 1 through 3, illustrated are three constructs of cooperating components of the system 10 for external fixation of bone according to the preferred embodiment of the present invention. In FIGS. 1A and 1B, a first construct of components of the system 10 is shown securing a fracture 12 of a bone 14. In particular, the system 10 is illustrated as being used to secure a bone fracture 12 of a tibia 14. The system 10 is used to secure the bone portions 16 and 18 in a fixed relationship so as to permit the fractured portions to fuse properly. FIG. 2 illustrates a second construct of the system 10 shown operatively attached to the tibia 14. In FIG. 3, a third construct of the system 10 is illustrated attached to the tibia 14. While the system 10 is shown throughout FIGS. 1 through 3 in conjunction with a tibia 14, it will be appreciated that the system 10 may be used with other bones as well. It will also be appreciated that the three constructions illustrated in FIGS. 1 through 3 are merely exemplary applications.

The structure and function of the individual cooperating components of the system 10 will be described with general reference to FIGS. 1 through 15. The components of the present invention are illustrated to generally include a universal clamp assembly 20, bar-to-bar clamp body 22, a three pin clamp assembly 24, a five pin clamp assembly 26, a telescoping post 28, a first ring connector assembly 30, a second ring connector assembly 32, a bone pin clamp body 34, and a post assembly 36. The components are illustrated to additionally include a compression/distraction arrangement 38 including a pair of clamping assemblies 40 and an externally threaded drive rod 42. Further, the components include a variable connector body 44, a ring assembly 46, and a plurality of cylindrical, smooth support rods 48. The support rods 48 include main support rods which are typically oriented to extend generally parallel to the axis of the bone 14 or at an acute angle relative to the bone 14 and supplemental support rods. The supplemental support rods 48', one of which is shown in FIG. 1B, may be provided in various lengths.

As will become apparent below, the components of the system 10 of the present invention may be combined in an infinite number of combinations and orientations to secure and rigidly interconnect a plurality of bone screws or pins 50 which are engaged with the bone portions 16 and 18. This flexibility of the system 10 permits a surgeon to independently place a bone screw 50 at a limitless number of positions along the bone 14 or angular orientations with respect to the bone 14.

Figure 4A:
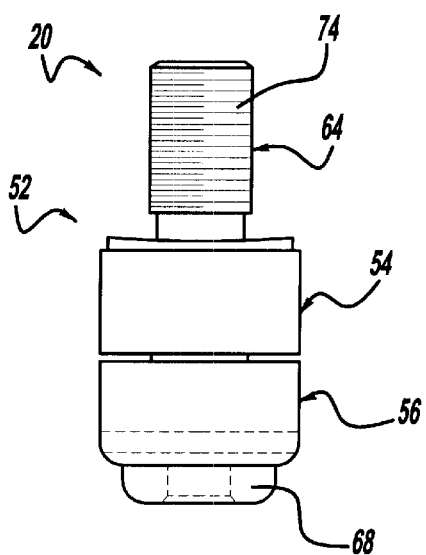
FIGS. 4A and 4B are views of a universal clamp assembly of the external fixation system according to the teachings of the preferred embodiment of the present invention.
Figure 4B:
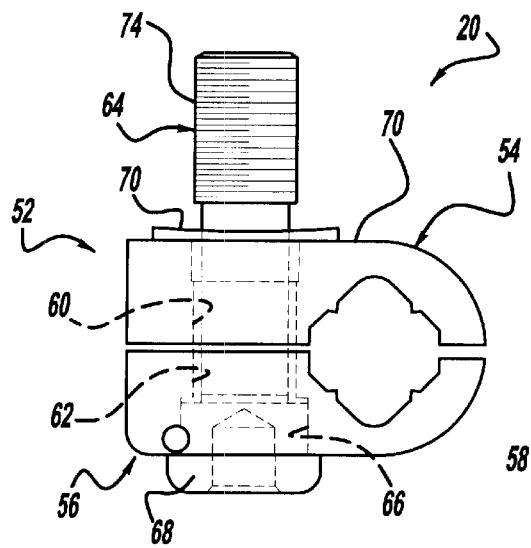

With reference to FIGS. 4A and 4B, the universal clamp assembly 20 of the present invention is illustrated. The universal clamp assembly 20 includes a clamp portion 52 having first and second halves 54 and 56 which cooperate to define a bar receiving aperture 58 for receiving one of the support rods 48, the telescoping post 28 or the post assembly 36. It will be understood that in the exemplary embodiment the support rods 48, telescoping post 28 and post assembly 36 each have a substantially identical diameter.

The first and second halves 54 and 56 include aligning apertures 60 and 62, respectively, for receiving a locking bolt or fastener 64. The aperture 62 of the second half 56 includes a counterbored portion 66 for receiving a portion of a head 68 of the fastener 64. An outer surface 70 of the first half 54 is formed to include a serrated portion 72 having a plurality of serrations radially extending from the opening of the aperture 60. The serrated portion 72 is adapted to engage substantially identical serrated portions provided on cooperating components of the system 10 of the present invention as will be discussed below.

An end 74 of the fastener 64 opposite the head 68 is externally threaded. When the fastener 64 engages an internally threaded aperture of a cooperating component and is rotated to draw the cooperating component against the first half 56, the first and second halves 56 of the clamp portion 52 are drawn together to thereby securely clamp one of the support rods 48, for example, within the aperture 58. The rod receiving aperture 58 is sized to receive one of the support rods 48, the telescoping post 28 or the post assembly 36.

The universal base clamp 20 is the fundamental component of the system 10 of the present invention. The universal base clamp 20 is designed to be easily placed anywhere along a support rod 48, for example (even between two previously locked universal base clamps 20). This can be cone by sliding the first half 54 up the fastener 64 and then rotating the first half 54 ninety degrees. This feature allows a surgeon to add components during the application without the inconvenience of unlocking clamps 20 already in place.

Figure 5A:
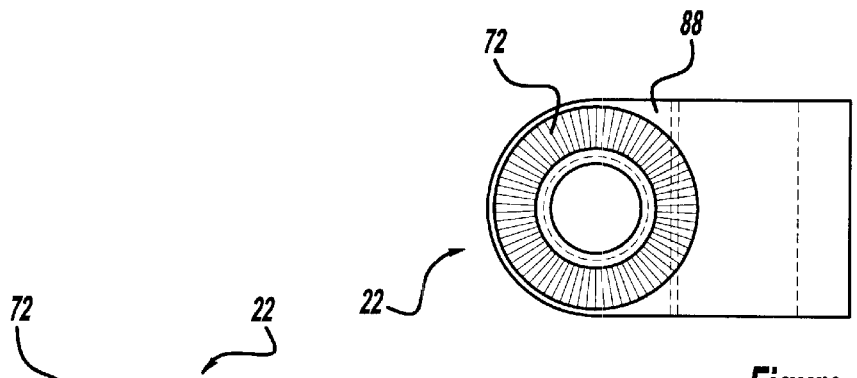
FIGS. 5A through 5C are views of a bar-to-bar clamp body of the external fixation system according to the teachings of the preferred embodiment of the present invention.
Figure 5B:
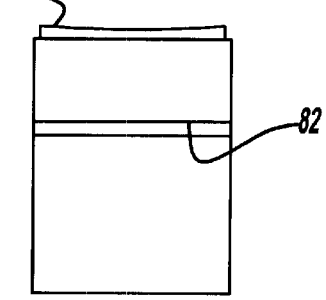
Figure 5C:
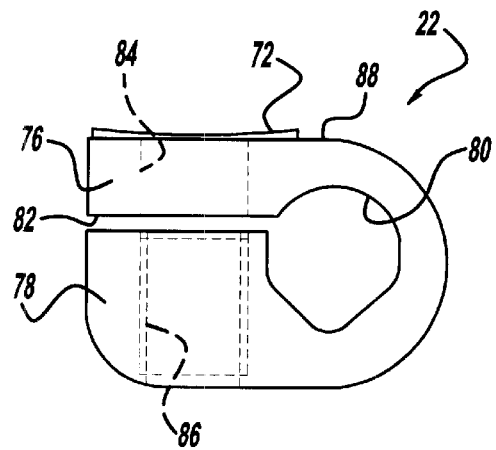

With reference to FIGS. 5A through 5C, the bar-to-bar clamp body 22 of the present invention is illustrated. The bar-to-bar clamp body 22 is generally C-shaped to define a rod receiving aperture 80 and includes first and second ends 76 and 78 which are spaced apart by an opening 82. The first and second ends 76 and 78 include aligning apertures 84 and 86, respectively, for receiving a fastener such as the fastener 64 described above with respect to the universal clamp assembly 20. The aperture 86 of the second end 78 is internally threaded. An outer surface 88 of the first end 76 is formed to include a serrated portion 72.

In use, the bar-to-bar clamp body 22 is attached to a cooperating component of the system 10 of the present invention through engagement of the fastener 64 with the apertures 84 and 86. In such engagement, the serrated portions 72 of the components are interlocked thereby preventing relative rotation. Tightening of the fastener 64 draws the ends 76 and 78 of the bar-to-bar clamp body 22 toward one another. As a result, a support rods 48, telescoping post 28 or post assembly 36 positioned within the aperture 80 is secured relative to the bar-to-bar clamp body 22 and in turn secured relative to the cooperating component.

Figure 6A:
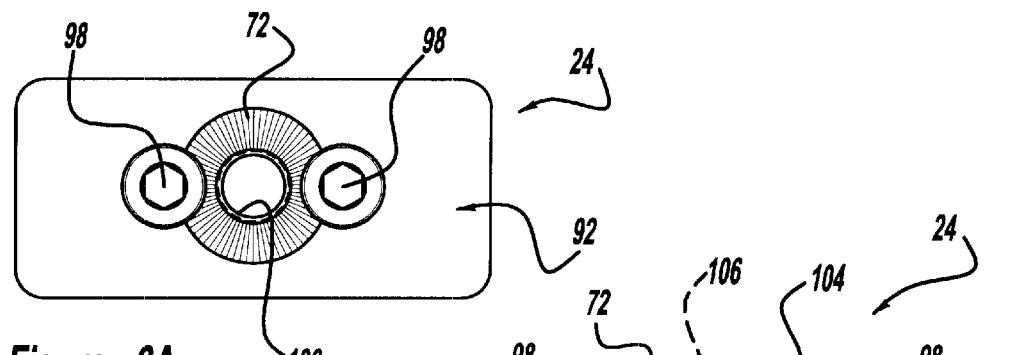
FIGS. 6A and 6B are views of a three pin clamp assembly of the external fixation system according to the teachings of the preferred embodiment of the present invention.
Figure 6B:
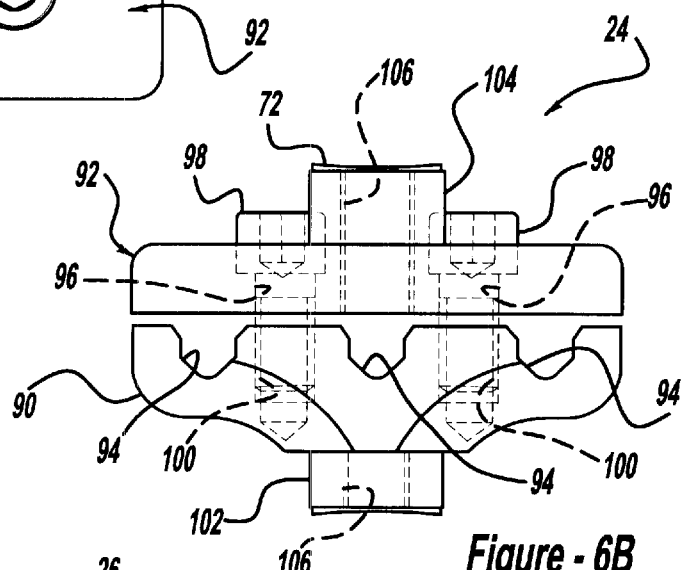

With reference to FIGS. 6A and 6B, the three pin clamp assembly 24 of the present invention is illustrated. The pin clamp assembly 24 is operative for receiving and securing up to three bone pins 50 engaged with the bone 14. The bone pin clamp 28 includes a main body member 90 and a cover pin member 92. The main body member 90 defines three bone pin rests 94. The bone pin rests or grooves 94 are substantially V-shaped and are operable to engage the sides of the bone pins 50.

The cover member 92 of the pin clamp assembly 24 is able to be inserted over the bone pins 50 when the bone pins 50 are located in the grooves 94. The cover member 92 includes a pair of apertures 96 which each allow a threaded fastener 98 to pass through the cover member 32 and into a threaded aperture 100 of the main body member 90. Tightening of the fasteners 98 rotationally and longitudinally secures the bone pins 50 relative to the pin clamp assembly 24.

To facilitate secure attachment of the pin clamp assembly 24 to other cooperating components of the system 10 of the present invention, the base member 90 and the cover member 92 are both formed to integrally include cylindrical extensions 102 and 104, respectfully. The ends of each of the cylindrical extensions 102 and 104 are both formed to include a serrated portion 72. Each of the cylindrical extensions 102 and 104 includes an internally threaded aperture 106 sized to receive a fastener 64.

Figure 7A:
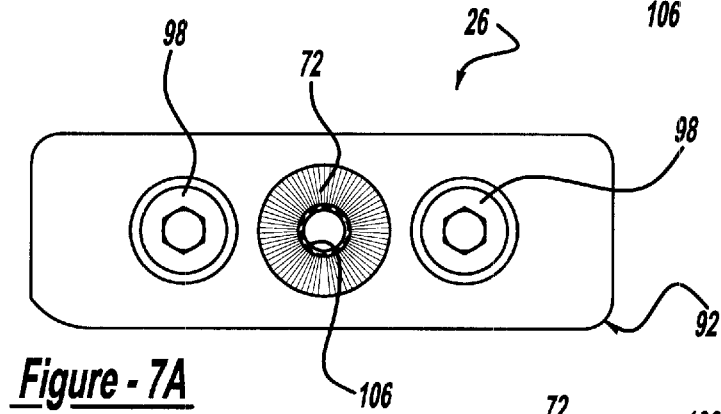
FIGS. 7A and 7B are views of a five pin clamp assembly of the external fixation system according to the teachings of the preferred embodiment of the present invention.
Figure 7B:
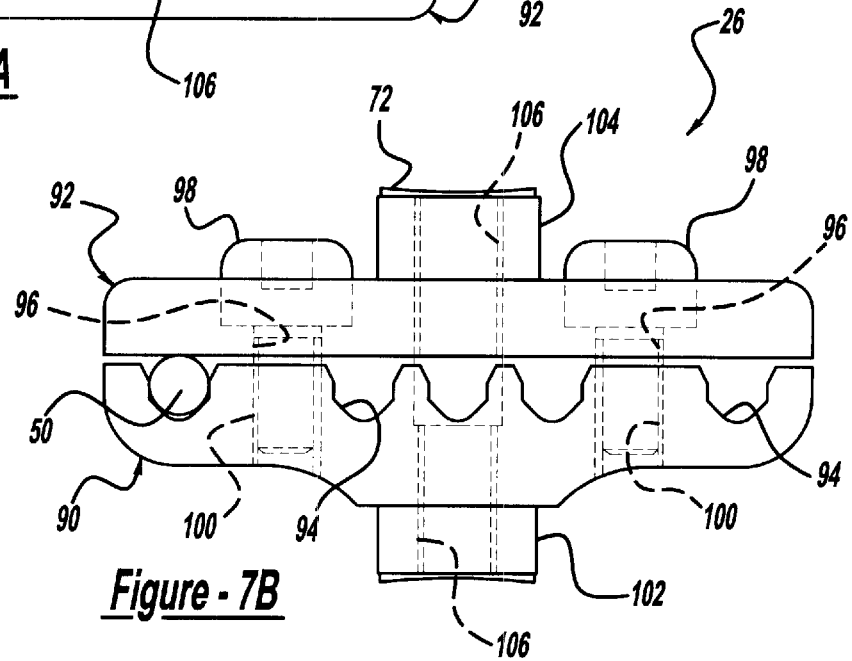

The five pin clamp assembly 26 is shown particularly in FIGS. 7A and 7B. The construction of the five pin clamp assembly 26 is identical to the construction of the three pin clamp assembly 26, with the exception that the five pin clamp assembly 26 is formed to include two additional bone pin rests 94. In this regard, the five pin clamp assembly 26 includes three bone pin rests 94 between the fasteners 98, whereas the three pin clamp assembly 24 includes a single bone pin rest 94 between the fasteners. Due to the similarity between the two pin clamp assemblies 24 and 26, like reference numbers are used in the drawings.

Figure 8A:
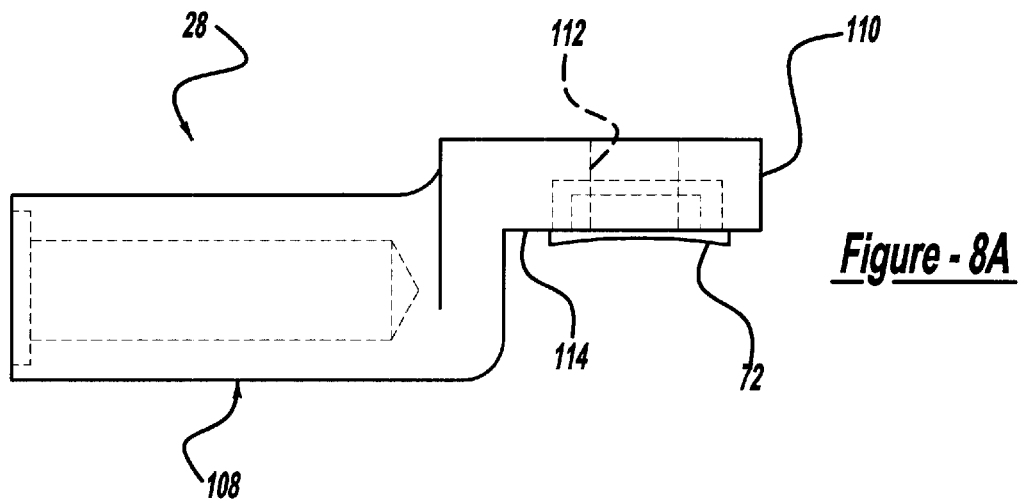
FIGS. 8A and 8B are views of a telescoping post of the external fixation system according to the teachings of the preferred embodiment of the present invention.
Figure 8B:
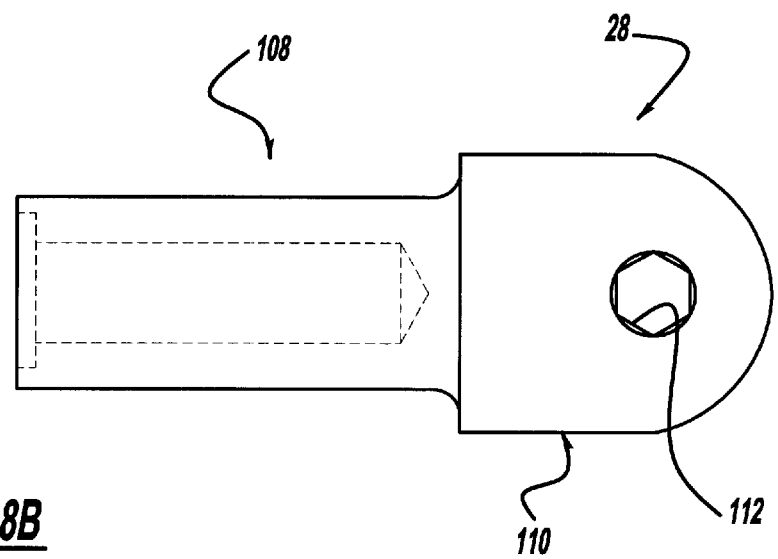

Turning now to FIGS. 8A and 8B, the telescoping post 28 of the present invention is illustrated. The telescoping post 28 includes a cylindrical post portion 108 and a mounting flange portion 110. The cylindrical post portion 108 has a diameter substantially equal to the diameter of the support rods 48 and thereby may be securely received within rod receiving apertures of cooperating components of the system 10 of the present invention. The mounting flange portion 110 includes an aperture 112 for receiving a fastener 64. A lower side 114 of the mounting flange portion 110 includes a serrated portion 72 for cooperating with the serrated portions of cooperating components of the system 10 in a manner discussed above.

Figure 9A:
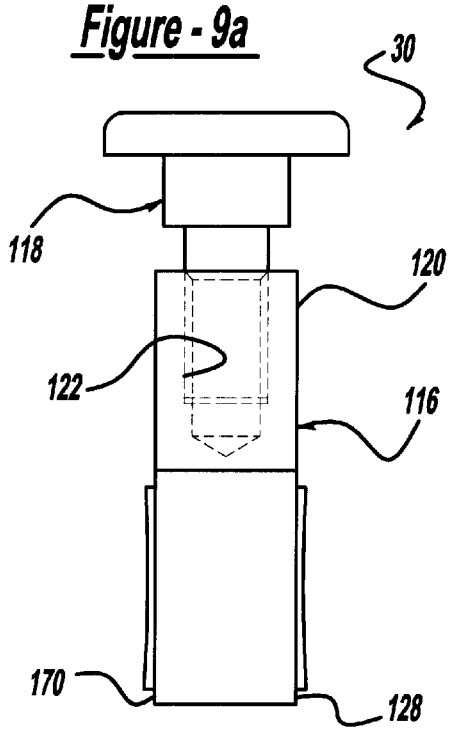
FIGS. 9A and 9B are views of a first ring connector assembly of the external fixation system according to the teachings of the preferred embodiment of the present invention.
Figure 9B:
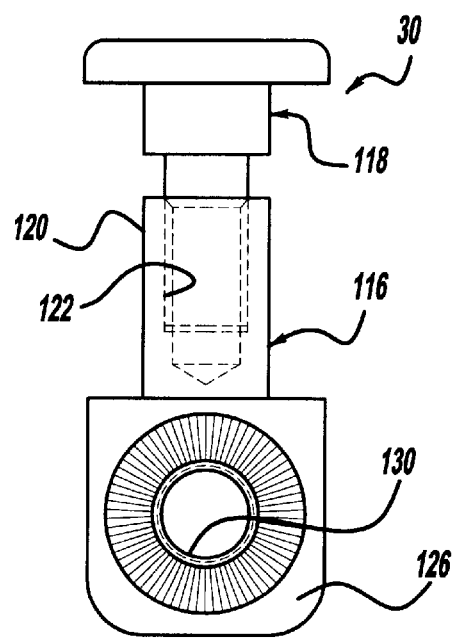

With reference to FIGS. 9A and 9B, the first ring connector assembly 30 of the present invention is illustrated. The first ring connector assembly includes a main body 116 and a fastener 118. An upper portion 120 of the main body 116 defines a vertically extending aperture 122 which is internally threaded to receive the externally threaded fastener 118. A lower portion 124 of the main body 116 includes a pair of spaced apart sides 126 and 128 and an aperture 130 horizontally passing therethrough. Both of the sides 126 and 128 are formed to include a serrated portion 72 radially surrounding the aperture 130 which is adapted to interface with cooperating components of the system 10 including a serrated portion 72 in a manner discussed above. The fastener 118 is adapted to pass through one of a plurality of apertures formed in a frame 132 of the ring assembly 46 for securing the first ring connector assembly 32 thereto.

Figure 10A:
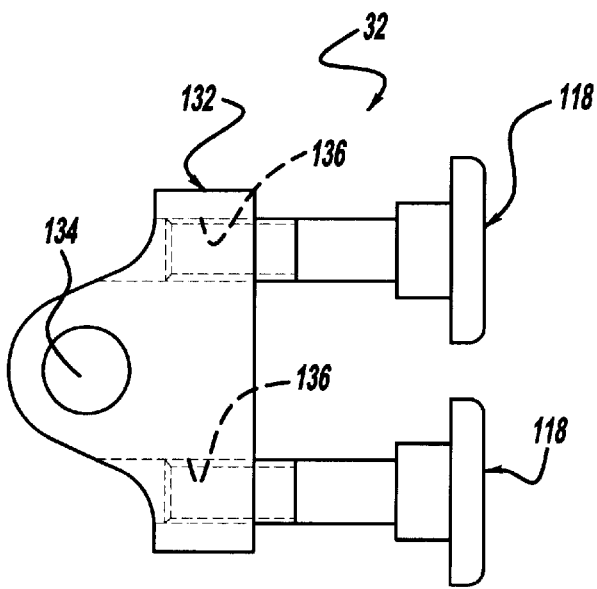
FIGS. 10A and 10B are views of a second ring connector assembly of the external fixation system according to the teachings of the preferred embodiment of the present invention.
Figure 10B:
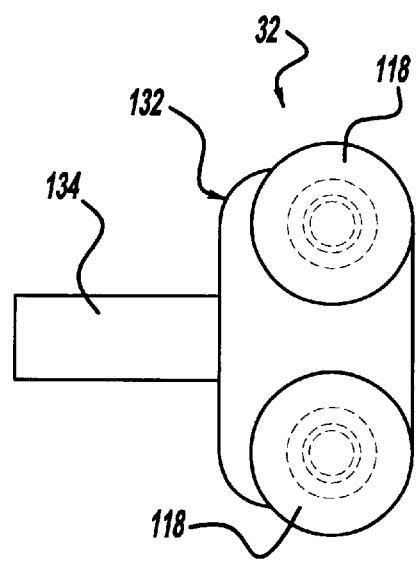

With reference to FIGS. 10A and 10B, the second ring connector assembly 32 of the present invention is illustrated. Rather than interfacing with cooperating components of the system 10 including a serrated portion 72, the second ring connector assembly 32 is adapted to interface with cooperating components including a rod receiving aperture, such as the universal clamp assembly 20 and the bar-to-bar clamp body 22. The second ring connector assembly 32 includes a main body portion 132 and a cylindrical extension 134. To facilitate clamping within one of the rod receiving apertures, the cylindrical extension 134 has a diameter substantially equal to the support rods 48. The main body 132 defines a pair of apertures 136 which are internally threaded for receiving a pair of threaded fasteners 118 identical to the fastener described with respect to the first ring connector assembly 30. In a similar manner, the fasteners 118 are adapted to pass through a pair of the plurality of apertures formed in the frame 132 of the ring assembly 46 for securing the second ring connector assembly thereto.

With reference to FIGS. 11A through 11D, the bone pin clamp body 34 of the present invention is illustrated. The bone pin clamp body 34 defines an aperture 138 for receiving a bone pin 50. The pin clamp body 34 includes an upper flange portion 140 and a lower flange portion 142 which are separated by a gap 144. The gap 144 intersects the aperture 138. The upper and lower flange portions 140 and 142 are formed to include aligning apertures 146 and 148 for receiving a fastener 64. The aperture 148 of the lower flange portion 142 is internally threaded.

An upper surface 150 of the upper flange portion 140 includes a serrated portion 72 surrounding the aperture 146. The serrated portion 72 is adapted to interface with serrated portions of cooperating components of the system 10 of the present invention in a manner discussed above. When a cooperating component is secured to the bone pin clamp body 34 with a fastener 64, tightening of the fastener 64 causes the gap 144 between the upper and lower flange portions 140 and 142 to decrease and the aperture 138 to slightly constrict. As a result, a bone pin 50 disposed within the aperture 138 is longitudinally and rotationally fixed with respect to the bone pin clamp body 34.

Figure 12A:
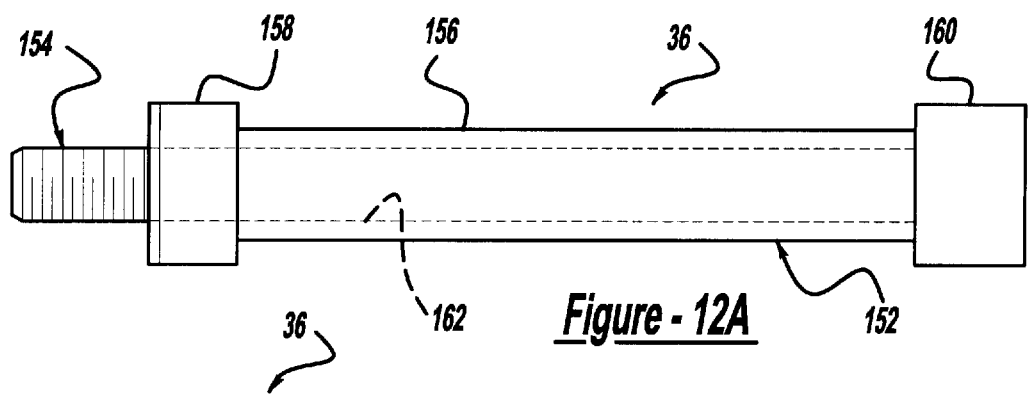
FIGS. 12A through 12C are views of a post assembly of the external fixation system according to the teachings of the preferred embodiment of the present invention.
Figure 12B:
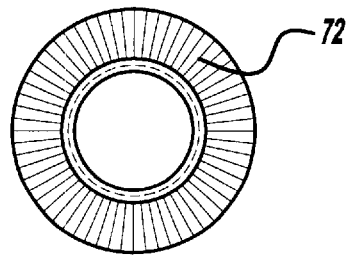
Figure 12C:
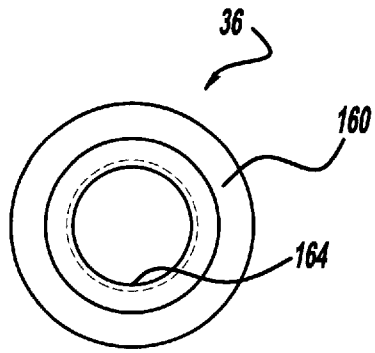

Turning now to FIGS. 12A through 12C, the post assembly 36 of the present invention is illustrated. The post assembly 36 generally includes a cylindrical sleeve 152 and a threaded fastener 154. The cylindrical sleeve 152 includes a central portion 156 and first and second enlarged ends 158 and 160. The cylindrical sleeve 152 has a diameter substantially equal to the diameter of the support rods 48 and can similarly interface with cooperating components including a rod receiving aperture, such as the universal clamp assembly 20, in a manner discussed above.

The cylindrical sleeve 152 defines an elongated aperture 162 for receiving the fastener 154. An outer end of the first enlarged end 158 includes a serrated portion 72 surrounding the aperture 162. The fastener 154 extends beyond the serrated portion and is externally threaded. An opposite end of the fastener 154 includes a recess 164 for receiving a tool (not shown) used to rotate the fastener 154 relative to the cylindrical sleeve 152. The serrated portion 72 is adapted to interface with serrated portions 72 of cooperating components of the system 10 of the present invention in a manner discussed above. The serrated portion 72 is particularly intended to cooperate with the 3 pin and 5 pin clamp assemblies.

Figure 14A:
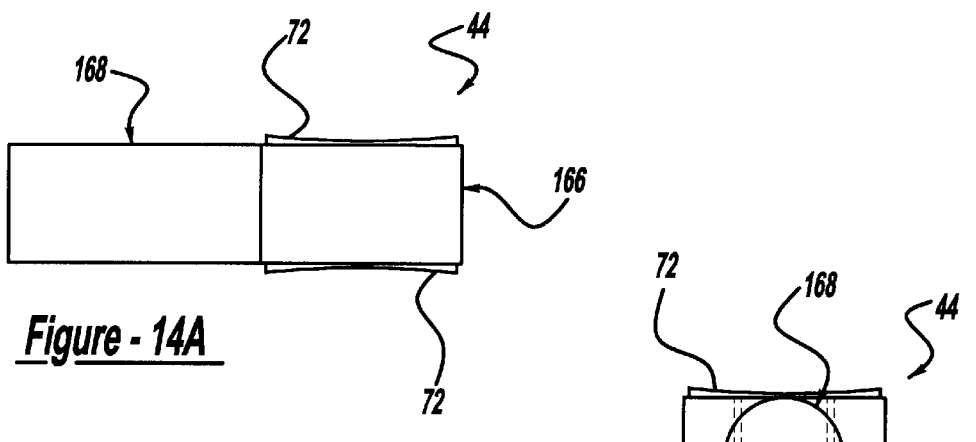
FIGS. 14A through 14C are views of a variable connector body of the external fixation system according to the teachings of the preferred embodiment of the present invention.
Figure 14B:
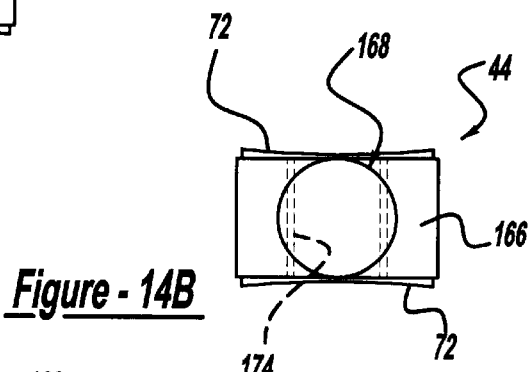
Figure 14C:
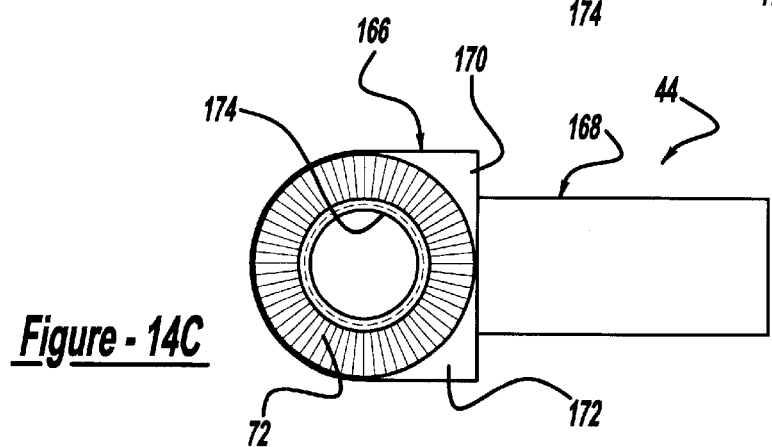
Figure 16:
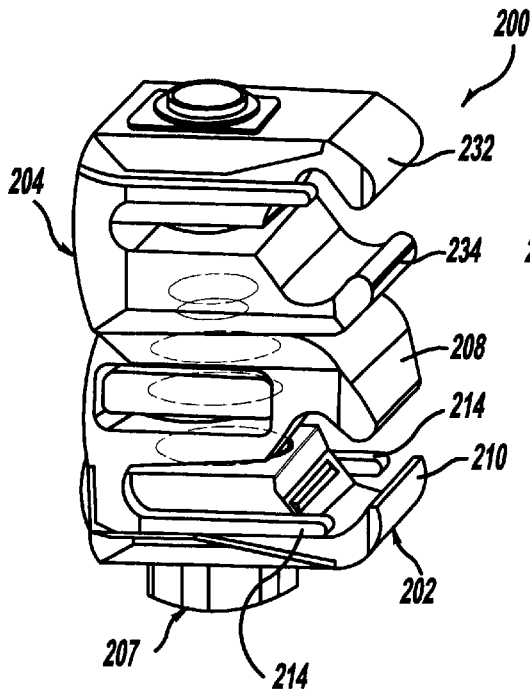
FIG. 16 is a perspective view of a clamp assembly according to the teachings of the preferred embodiment of the present invention, the clamp assembly adapted to receive first and second cylindrical rods.
Figure 17:
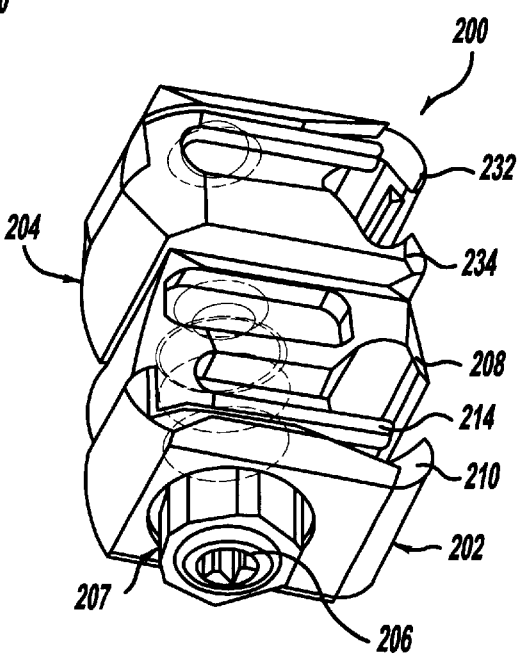
FIG. 17 is another perspective view of the clamp assembly according to the teachings of the preferred embodiment of the present invention.
Figure 18:
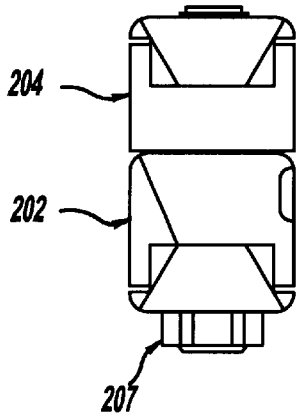
FIG. 18 is a rear view of the clamp assembly according to the teachings of the preferred embodiment of the present invention.
Figure 19:
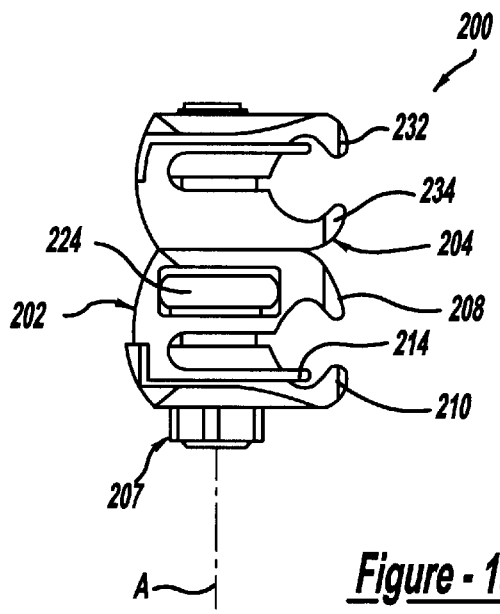
FIG. 19 is a side view of the clamp assembly according to the teachings of the preferred embodiment of the present invention.

With reference to FIGS. 14A through 14C the variable connector body 44 of the present invention will be described. The variable connector body 44 generally includes a main body 166 and a cylindrical portion 168 extending from the main body 166. The main body 166 includes a pair of spaced apart sides 170 and 172 and an internally threaded aperture 174 passing therethrough. Both of the sides 170 and 172 are formed to include a serrated portion 72 radially surrounding the aperture 174 which is adapted to interface with cooperating components of the system 10 including a serrated portion 72 in a manner discussed above. The cylindrical portion 168 has a diameter substantially equal to the diameter of the support rods 48 and thereby may be securely received within rod receiving apertures of cooperating components of the system 10 of the present invention in a manner discussed above.

Figure 15:
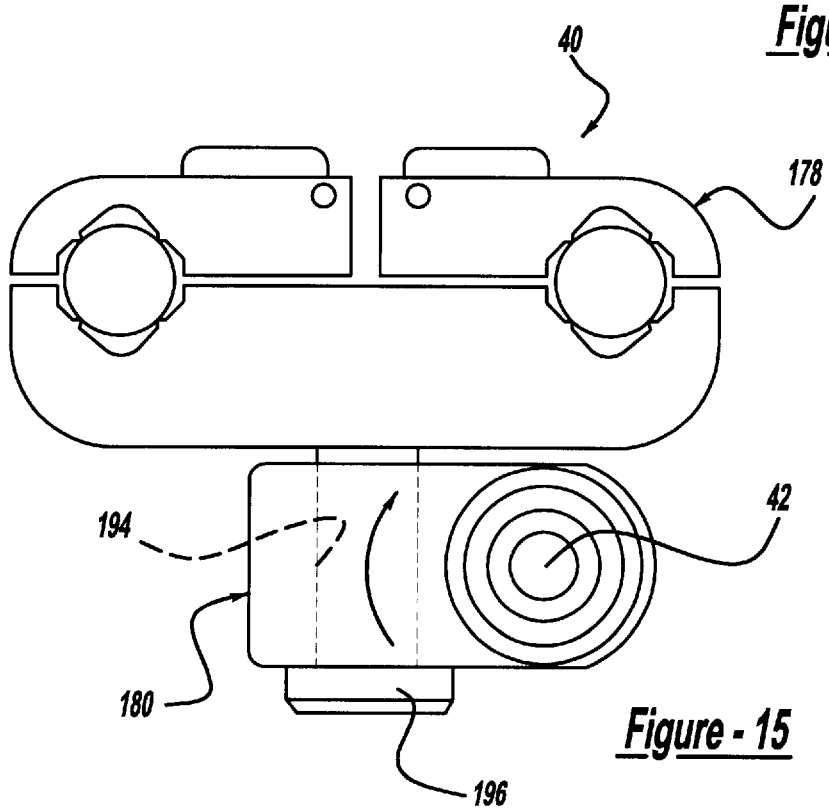
FIG. 15 is a side elevational view of the bar clamping unit and threaded rod receiving unit the compression/distraction assembly of the external fixation system according to the teachings of the preferred embodiment of the present invention.
Figure 13:
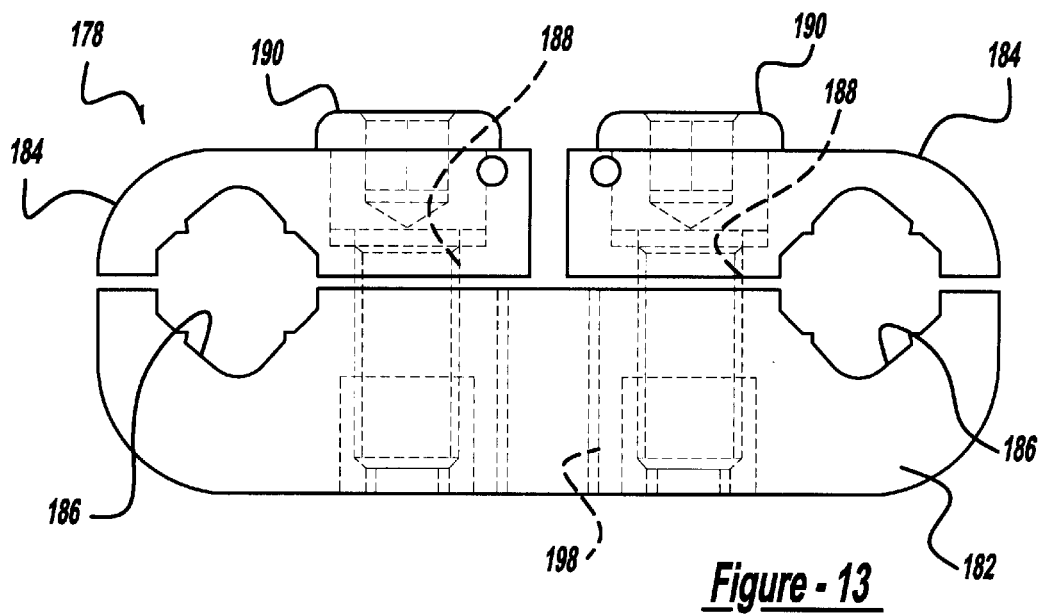
FIG. 13 is a side elevational view a bar clamping unit of a compression/distraction arrangement of the external fixation system according to the teachings of the preferred embodiment of the present invention.

With reference to FIGS. 13 and 15, the compression/distraction arrangement 38 of the present invention will be described. The clamping assemblies 40 of the distraction arrangement 38 each include a bar clamping unit 178 and a threaded rod receiving unit 180. The bar clamping unit 178 includes a lower portion 182 and a pair of substantially identical upper portions 184. Each of the upper portions 184 cooperates with the lower portion 182 to define an aperture 186 for receiving one of the support rods 48. The upper portions 184 each include an apertures 188 which each allow a threaded fastener 190 to pass therethrough and into an aligning threaded aperture 192 provided in the lower portion 182. Tightening of the fasteners 190 secures the support rods 48. When the bar clamping units 178 are used in tandem, a pair of the support rods 48 are non-rotatably retained in a parallel and spaced apart relationship.

The threaded rod receiving unit 180 of each of the clamping assemblies 40 includes a first aperture (not specifically shown) which is internally threaded for receiving the drive rod 42. The clamping assemblies 40 additionally include a second aperture 194 oriented substantially perpendicular to the first aperture. The second aperture 194 allows a threaded fastener 196 to pass therethrough and into an aligning internally threaded aperture 198 provided in the lower portion 182 of the bar clamping unit 178 for securing the bar clamping unit 178 to the threaded rod receiving unit 180.

When the compression/distraction arrangement 38 is incorporated into a construct, as shown in FIG. 2 for example, the threads of the apertures receiving the drive rod 42 progress in opposing directions. To operate the compression/distraction arrangement 38, the fastener 190 of a first one of the bar clamping units 178 which is associated with one of the support rods 48 must be loosened to permit the support rod 48 to slide within the aperture 186. Similarly, the fastener 190 of a second of the bar clamping units 178 which is associated with the other one of the support rods 48 must be loosened to permit the support rod 48 to slide in its aperture 186. In this manner, one of the bar clamping units 178 is permitted to translate with respect to one of the support rods 48 and the other of the clamping units 178 is permitted to translate relative to the other of the support rods 48. At this point, rotation of the drive rod 42 in a first direction causes relative movement between the clamping assemblies 40 such that they approach one another and the bone 14 is compressed. Conversely, rotation of the drive rod 42 in a second direction causes relative movement between the clamping assemblies 40 such that they diverge from one another and the bone 14 is distracted.

Figure 3A:
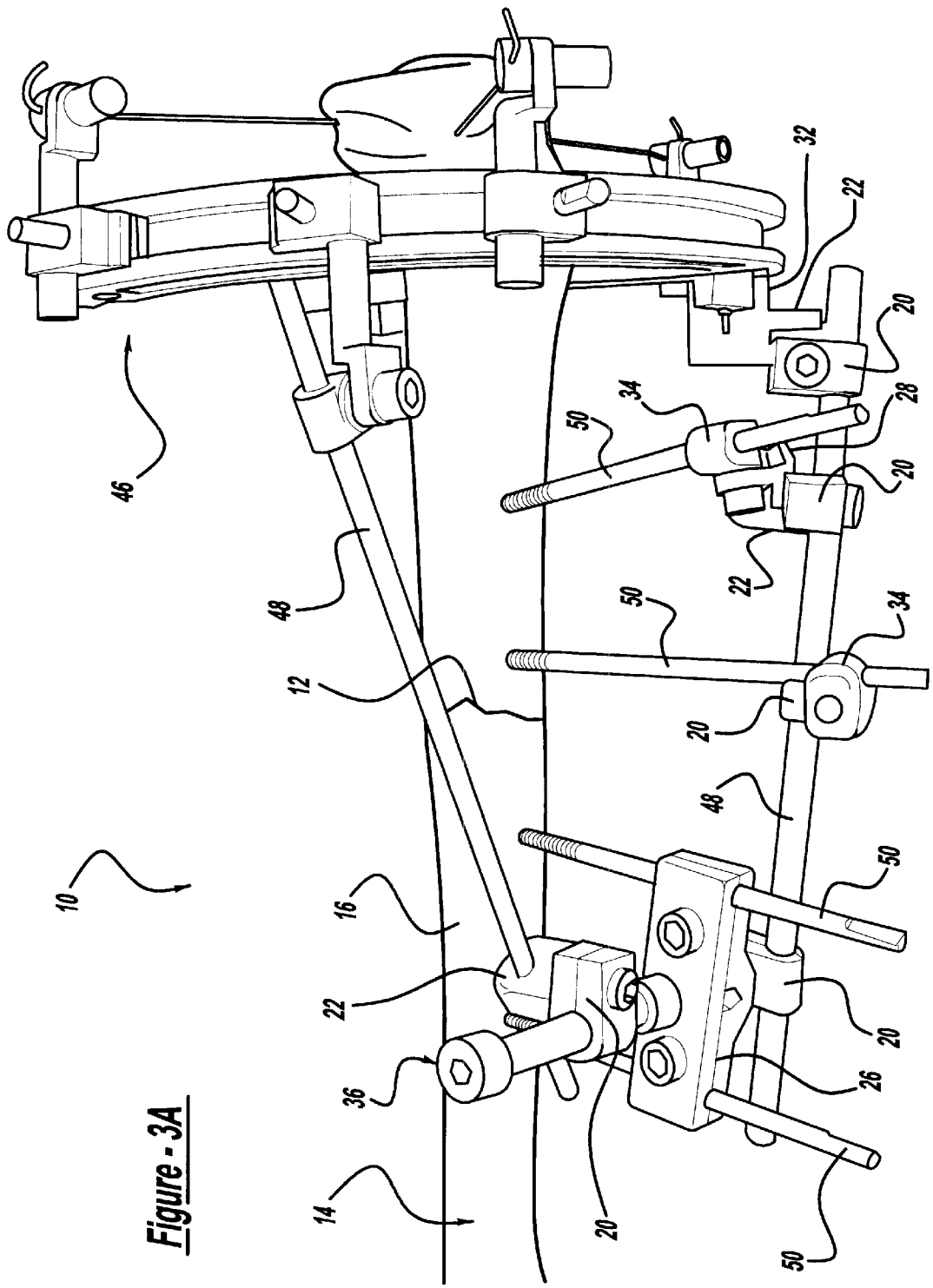
FIGS. 3A and 3B illustrate a third exemplary construct of components of the external fixation system according to the teachings of the preferred embodiment of the present invention in operative association with a tibia, the third construct incorporating a ring assembly.
Figure 3B:
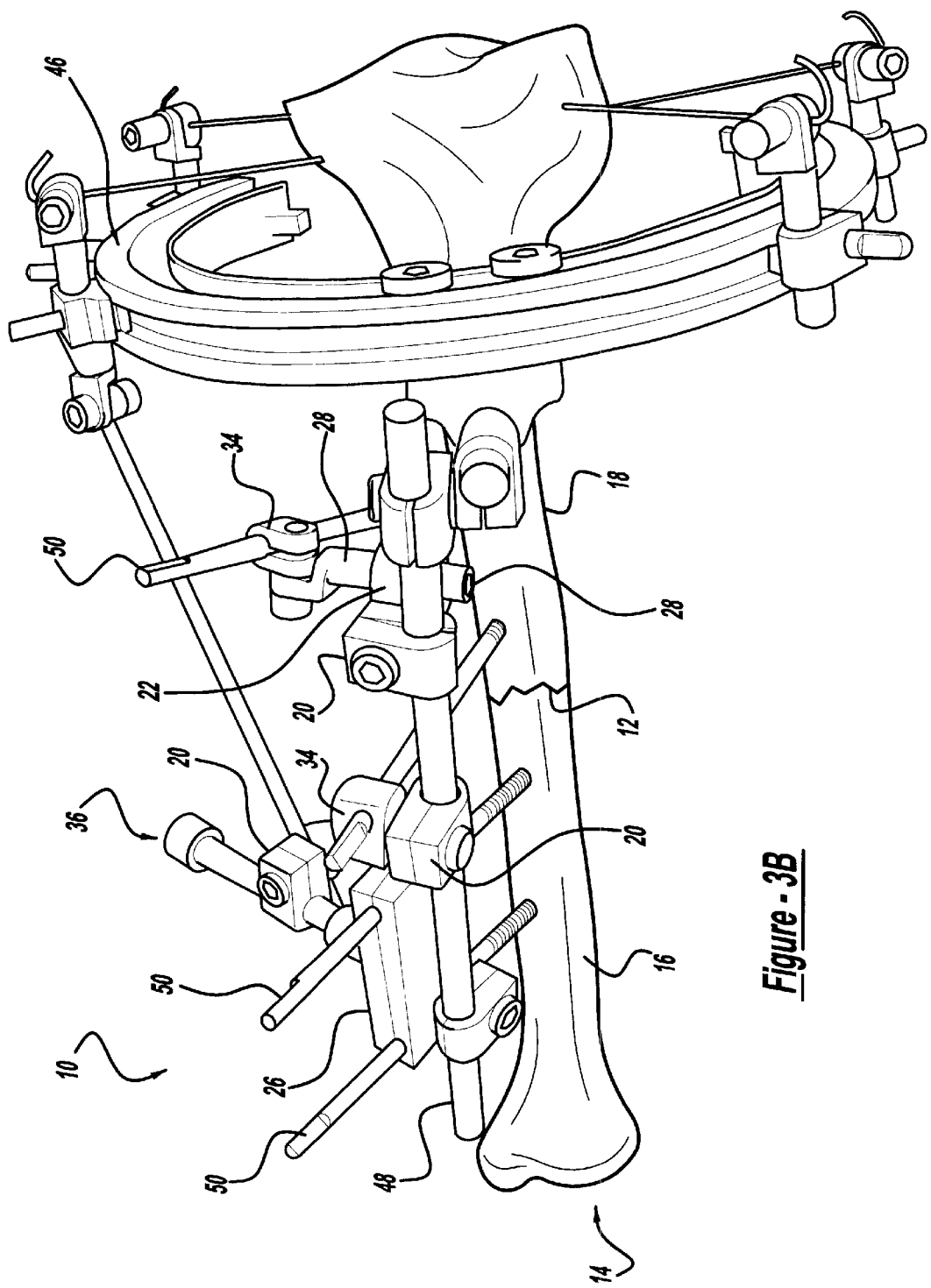

The ring assembly 46 of the present invention is shown in the exemplary construct of FIGS. 3A and 3B. A substantially identical ring assembly is shown and described in commonly assigned U.S. Ser. No. 09/086,256, filed Jun. 28, 1998. U.S. Ser. No. 09/086,256 is incorporated by reference as if fully set forth herein.

With reference now to FIGS. 16–32, a clamp assembly constructed in accordance with the teachings of the preferred embodiment of the present invention is illustrated and generally identified at reference item 200. The clamp assembly 200 is operative for connecting first and second elongated members. In the embodiment illustrated, the first and second elongated members are cylindrical in shape and identical to the support rods 48 discussed above.

The clamp assembly 200 is illustrated to include a first or lower clamp member 202 and a second or upper clamp member 204. Terms of orientation, including but not limited to such as "upper" and "lower" will be used herein for purposes of referencing the drawings and are not to be considered limiting. Explaining further, it will be readily apparent to those skilled in the art that the clamp assembly 200 is equally operative in any particular orientation and is not limited to the orientation shown in the drawings.

The first and second clamp members 202 and 204 are connected by a fastener 206 in a manner to be further discussed below. The fastener 206 is operative for locking the cylindrical rod 48 relative the second clamp member 204. The fastener 206 is further operative for arresting the relative angular orientations of the first and second clamp members 202 and 204 about an axis A (identified in FIG. 19) defined by the fastener 206. A second fastener 207 operates to lock a cylindrical rod 48 within the first clamp member 202.

The first clamp member 202 includes an upper jaw portion 208 and a lower jaw portion 210 which cooperate to define an opening 212 for receiving the cylindrical rod 48. The upper jaw portion 208 of the first clamp member 202 is formed to include a pair of spaced apart and cantilevered lever arms 214. The lever arms 214 are adapted to be resiliently deflected upon introduction of the cylindrical rod 48 into the opening 212. In this manner, the cylindrical rod 48 is temporarily held in place until the upper and lower jaw portions 208 and 210 are locked down.

The lower jaw portion 210 includes a reduced width portion 216 which is received between the cantilevered arms 214. In this manner, relative rotation between the upper and lower jaw portions 208 and 210 is prevented.

To provide means for fixedly locking the cylindrical rod 48 within the first clamp member 202, the fastener 207 extends through an aperture 220 (FIG. 22) provided in the lower jaw portion 210 and threadably engages an internally threaded aperture 222 formed in a locking plate 224 of the upper jaw portion 208. Explaining further, the upper jaw portion 208 defines a laterally extending slot 226 in which the locking plate 224 is disposed.

Figure 24:
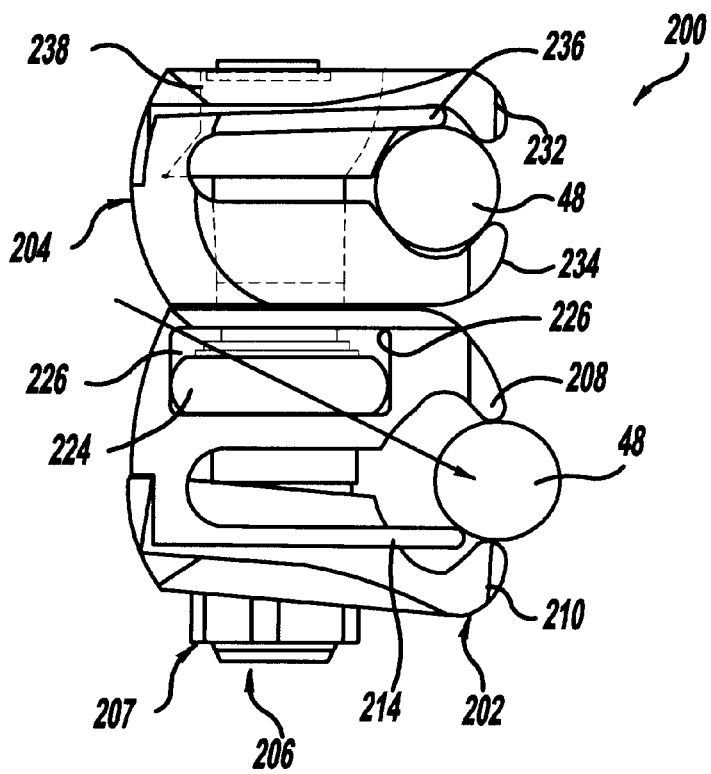
FIG. 24 is another side view similar to FIG. 19 illustrating a first cylindrical rod fully seated within the upper clamp member and a second cylindrical rod being introduced into a lower clamp member.

The fastener 207 preferably includes a spherically shaped portion 228 which is matingly received within a spherically shaped counterbored portion of the aperture 220. As shown most particularly in FIG. 31, an upper side of the aperture 220 includes a relieved portion 229 which accommodates pivoting of the lower jaw 210 on the fastener 207 as shown in FIG. 24, for example.

An end portion of the fastener 207 includes a hexagonally shaped surface 230 engageable by a conventional drive tool (such as a wrench or socket (not shown). When the fastener 207 is rotated clockwise, as identified by arrow B in FIG. 21, a threaded shaft 232 of the fastener 207 further engages the locking plate 224. In this manner, the lower jaw portion 210 is drawn towards the upper jaw portion 208 and the cylindrical rod 48 is captured therebetween.

The second clamp member 204 similarly includes an upper jaw portion 232 and a lower jaw portion 234. The upper jaw portion 232 of the second clamp member 204 is similar in construction and operation to the lower jaw member 210 of the first clamp member 202 and the lower jaw member 234 of the second clamp member 204 is similar in construction and operation to the upper jaw member 208 of the first clamp member 202. As with the upper jaw member 208, the lower jaw member 234 of the second coupling member 204 includes a pair of spaced apart and cantilevered lever arms 236. A cylindrical rod 48 is temporarily held in place through a snap-fit with the pair of lever arms 236. Aligning apertures 238 and 240 are provided in the upper and lower jaw portions 232 and 234 and receive a nut member 242 (shown particularly in FIG. 29). The nut member 242 has a generally rectangular end 244 with convexly curved opposing sides 246 and 248 connected by generally flat sides. The convexly curved opposing sides 246 and 248 are matingly received within the aperture 238 of the upper jaw portion 232. Similar to the aperture 220 of the lower jaw portion 210 of the first clamp member 202, the aperture 238 includes a relieved portion which accommodates pivoting of the upper jaw portion 232 about the axis A (identified in FIG. 19) as shown in FIG. 22. The rectangular shape of the aperture 238 limits the pivoting movement of the upper jaw portion 232 to a single plane.

A cylindrical portion 250 of the nut member 242 is received within the cylindrical aperture 240 of the lower jaw portion 234. The nut member 242 defines an internally threaded aperture 252 for receiving an externally threaded end 254 of the fastener 206.

In the preferred embodiment, the fastener 207 is hollow and defines a longitudinal channel 256 for receiving the fastener 206 in a co-axial arrangement. The fastener 206 is formed to include a hexagonal shaped recess 258 at either end such that the fastener 206 can be rotated from either end with a conventional drive tool (not shown). When the fastener 206 is rotated clockwise from its lower end (as indicated by arrow B in FIG. 21) or counterclockwise from its upper end (as indicated by arrow C in FIG. 20), the upper jaw portion 232 is drawn down against the lower jaw portion 234 and the cylindrical rod 48 is captured therebetween.

To provide means for arresting angular movement of the first clamp member 202 relative to the second coupler 204 about the axis A of the fastener 206, the first and second clamp members 202 and 204 are formed to include cooperating serrations. As particular shown in FIG. 30, an upper surface 260 of the first coupler 202 includes a serrated portion 262 having a plurality of serrations radially extending from an aperture 264. The serrated portion 262 is adapted to engage a substantially identical serrated portion (not particularly shown) provided on an adjacent lower surface of the second clamp member 204. When the fastener 206 is initially tightened, the serrated portions 262 of the first and second clamp members 202 and 204 are drawn together to prevent relative movement therebetween. Further tightening of the fastener 206 draws the upper and lower jaw portions 232 and 234 of the second clamp member 204 together to secure the cylindrical rod 48.

Use of the clamp assembly 200 will now be summarized. As shown in FIG. 22, a first cylindrical rod is introduced between the first and second jaw portions 232 and 234 of the second clamp member 204. The cylindrical rod 48 exerts a force on the lever arms 236 to thereby upwardly displace the lever arms 236. A counter-force snapingly retains the cylindrical rod temporarily in place. FIG. 23 shows the cylindrical rod in a seated position within the second clamp member 204. As illustrated, the lever arms 236 remain bent and maintain a force on the rod 48 to prevent it from falling out of the clamp assembly 200.

Figure 25:
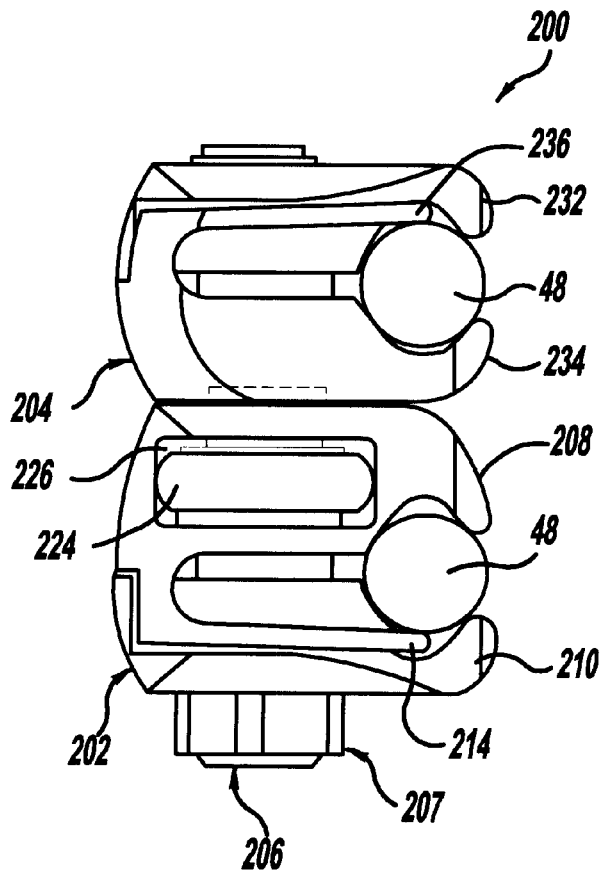
FIG. 25 is another side view similar to FIG. 19 illustrating the first and second cylindrical rods fully seated within the upper and lower clamp members, respectively, the upper and lower clamp members restrained from relative angular movement with respect to each other about an axis defined by a connecting fastener.

As shown in FIGS. 24 and 25, a second cylindrical rod is similarly inserted between the jaw portions 208 and 210 of the first clamp member 202.

Figure 25A:
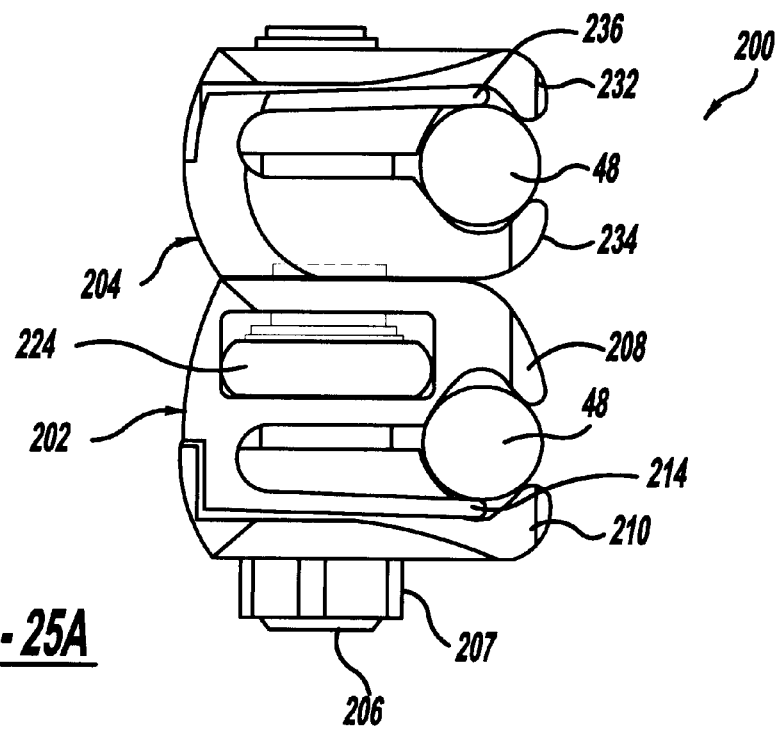
FIG. 25A is a side view similar to FIG. 25 illustrating locking of one of the cylindrical rods relative to the lower clamp member.

With particular reference to FIG. 25A, the fastener 207 has been tightened such that the locking plate 204 has been drawn downward to correspondingly cause the upper jaw member 208 to be drawn down against the lower jaw member 210 and lock the cylindrical rod 48 therebetween. Additionally, the fastener 206 has been initially tightened such that the first and second clamp members 202 and 204 are drawn together and the cooperating serrations 262 prevent relative rotation therebetween. In this condition, the clamp assembly 200 can be used for bone lengthening. Explaining further, the upper cylindrical rod 48 can be moved relative to the lower cylindrical rod 48 without losing the position of the first clamp member 202 or the angle between the first and second clamp members 202 and 204.

Figure 26:
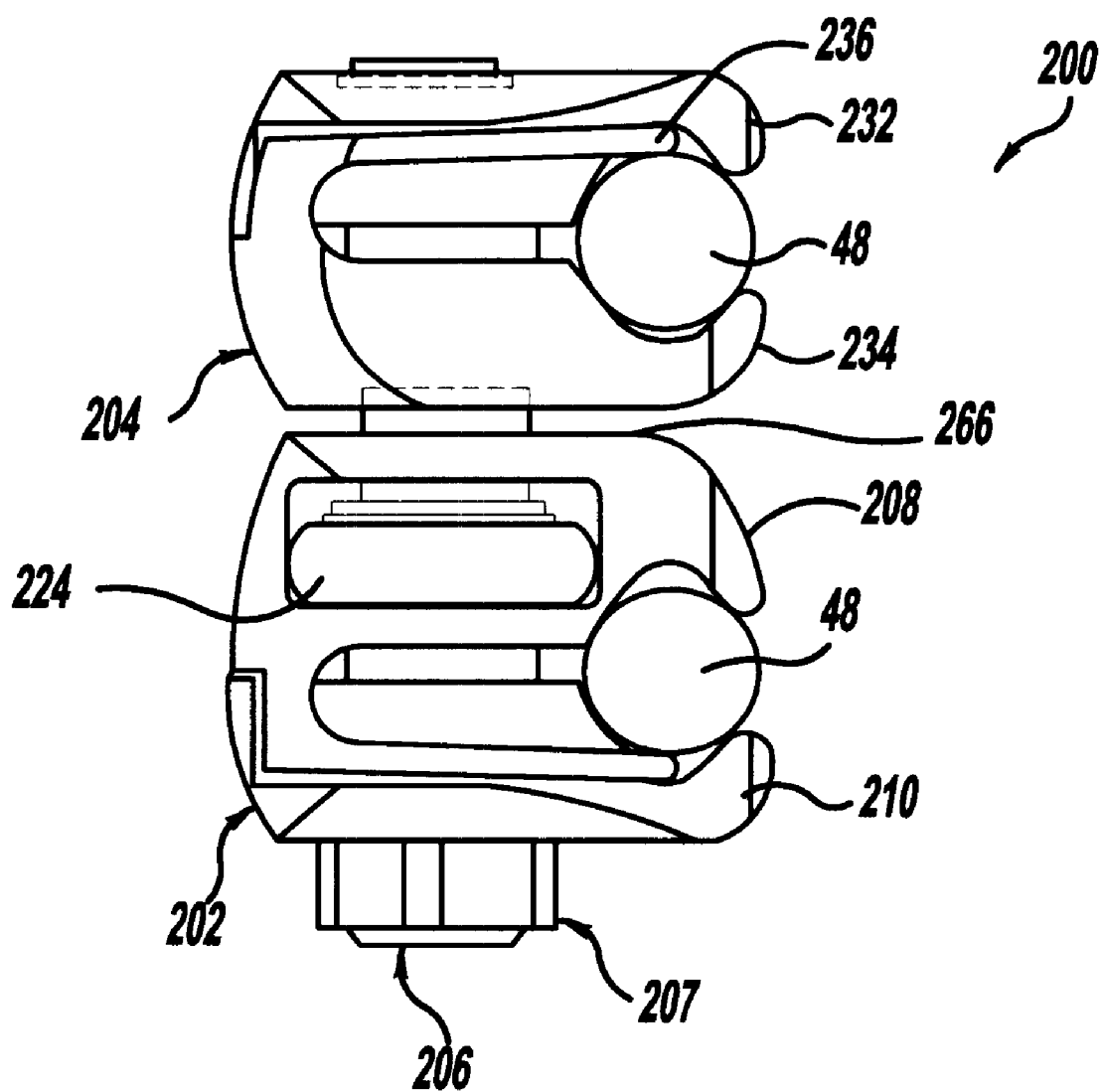
FIG. 26 is a side view similar to FIG. 25 illustrating the upper and lower clamp members separated from one another so as permit relative angular rotation about the axis defined by the connecting fastener.
Figure 27:
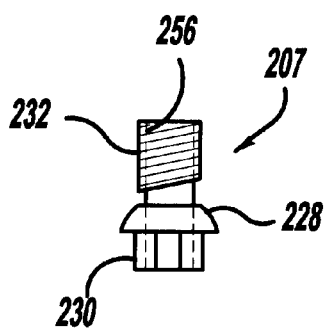
FIG. 27 is a side view of a fastener of the clamp assembly according to the teachings of the preferred embodiment of the present invention operative for engaging a locking plate and rigidly locking the cylindrical rod within the lower clamp member.
Figure 28:
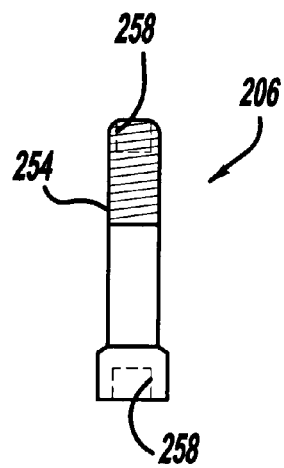
FIG. 28 is a side view of a fastener of the fastener connecting the upper and lower clamp members.
Figure 29:
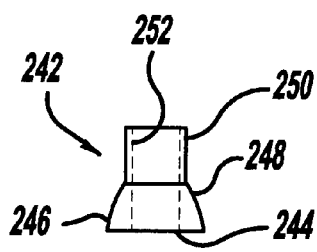
FIG. 29 is a side view of a nut for receiving the fastener connecting the upper and lower clamp members according to the teachings of the preferred embodiment of the present invention.
Figure 30:
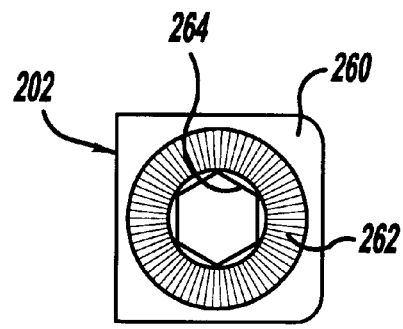
FIG. 30 is a top view of the lower clamp member.
Figure 31:
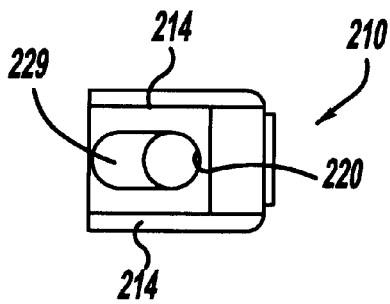
FIG. 31 is a top view of a lower jaw member of the lower clamp member.
Figure 32:
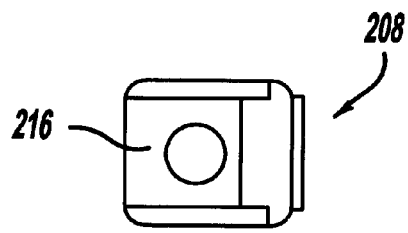
FIG. 32 is a bottom view of an upper jaw member of the lower clamp member.

The clamp assembly 200 is illustrated in FIG. 26 with the fastener 206 fully loosen. In this position, a gap 266 exists between the first and second clamp members 202 and 204 and the corresponding plurality of serrations 262 are separated. As such, the first and second clamp members 202 and 204 can be rotated relative to one another about the axis A.

Figure 33:
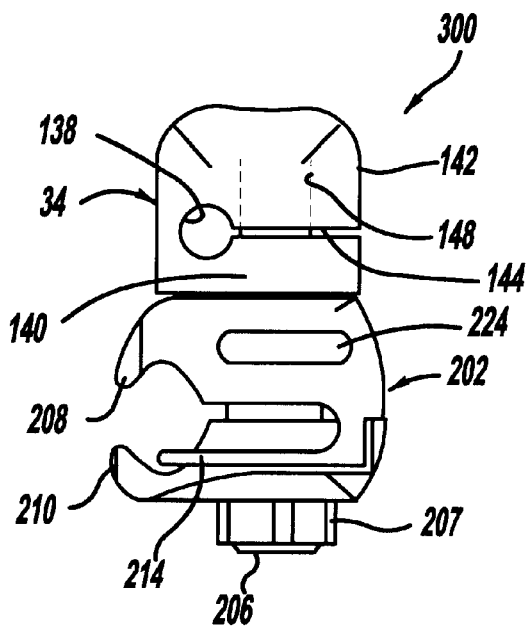
FIG. 33 is a side view of a second clamp assembly constructed in accordance with the teachings of the preferred embodiment of the present invention, the second clamp assembly specifically adapted for connecting a cylindrical rod and a bone pin.
Figure 34:
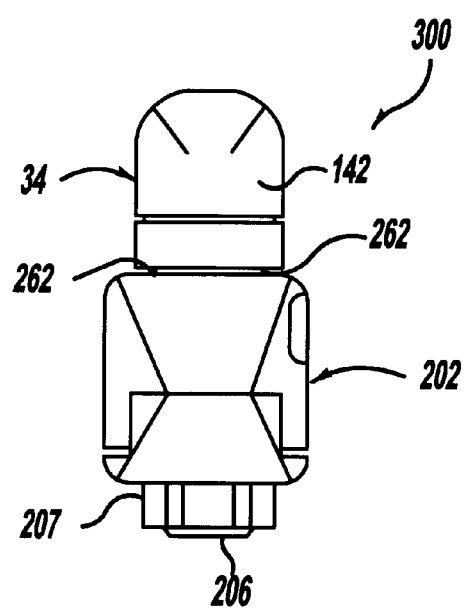
FIG. 34 is a rear view of the clamp assembly of FIG. 30.

Turning now to FIGS. 33 and 34, a variation of the clamp assembly 200 is illustrated. More particularly, a clamp assembly 300 is illustrated for connecting a bone screw or pin 50 and a cylindrical rod 48. The clamp assembly 300 is illustrated to include the bone pin clamp body 34 described above with particular reference to FIGS. 11A–11D and the first clamp member 202 of the clamp assembly 200. The fasteners 206 and 207 are employed in much the same manner discussed above with respect to the clamp assembly 200. Briefly, the fastener 206 threadably engages the locking plate 204 such that tightening of the fastener 207 draws the locking plate downward and correspondingly draws the upper jaw portion 208 towards the lower jaw portion 210 to lockingly capture a cylindrical rod 48 therebetween. The lever arms 214 of the first clamp member 202 operate in the manner discussed above to temporarily retain the cylindrical rod 48. The fastener 206 extends through the fastener 207 and threadably engages an internally threaded aperture 148 of the flange portion 142 of the pin clamp body 34. Initial tightening of the fastener 206 draws the pin clamp body 34 toward the first clamp member 202 such that adjacent serrations 262 of the components engage and prevent relative rotation. Further rotation of the fastener 206 causes the gap 144 between the flange portions 140 and 142 to decrease the aperture 138 to slightly constrict. As a result, the bone pin 50 disposed with the aperture 138 is longitudinally and rotationally fixed with respect to the bone pin clamp body 34.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. A clamp assembly of an external fixation system for connecting first and second elongated members, the clamp assembly comprising:

a first clamp member for engaging the first elongated member, the first clamp member including a first jaw portion and a second jaw portion, the first and second jaw portions at least partially defining a laterally extending channel for receiving the first elongated member, the first jaw portion including at least one cantilevered arm extending substantially perpendicular to the channel, the at least one cantilevered arm being resiliently displaceable through elastic deformation of the first clamp member upon introduction of the first elongated rod into the channel such that the at least one cantilevered arm temporarily retains the first elongated rod in the channel.

2. The clamp assembly of an external fixation system for connecting first and second elongated members of claim 1, wherein the at least one cantilevered arm includes a pair of cantilevered arms.

3. The clamp assembly of an external fixation system for connecting first and second elongated members of claim 2, wherein the at least one cantilevered arm is connected to the first jaw portion through a hinge portion.

4. The clamp assembly of an external fixation system for connecting first and second elongated members of claim 2, wherein the second jaw portion is positioned laterally between the pair of cantilevered arms.

5. The clamp assembly of an external fixation system for connecting first and second elongated members of claim 1, wherein the at least one cantilevered arm is integrally formed with the first jaw portion and the elongated rod is received between the first jaw portion and the at least one cantilevered arm.

6. The clamp assembly of an external fixation system for connecting first and second elongated members of claim 1, wherein the first clamp member further comprises a first fastener connecting the first and second jaw portions.

7. The clamp assembly of an external fixation system for connecting first and second elongated members of claim 6, wherein the first fastener passes through an aperture provided in the first jaw portion and threadably engages the second jaw portion such that rotation of the first fastener in a first direction draws the first and second jaw portions together.

8. The clamp assembly of an external fixation system for connecting first and second elongated members of claim 7, further comprising:

a second clamp member having first and second jaw portions at least partially defining a laterally extending channel for receiving a second elongated rod; and a second fastener connecting the first and second clamp members, wherein rotation of the second fastener in the first direction draws the first and second jaw portions of the second clamp member together.

9. The clamp assembly of an external fixation system for connecting first and second elongated members of claim 8, wherein the first and second fasteners are substantially co-linear.

10. The clamp assembly of an external fixation system for connecting first and second elongated members of claim 8, wherein the first fastener is hollow and the second fastener passes through the first fastener.

11. A clamp assembly of an external fixation system for connecting first and second elongated members, the clamp assembly comprising:

a first clamp member including first and jaw portion for engaging a first elongated rod, the first clamp member operative in an unclamped mode such that the first elongated rod can translate along its axis relative to the first clamp member and a clamped mode such that movement of the first elongated rod relative to the first clamp member is arrested;

a second clamp member including first and second jaw portion for engaging a second elongate rod, the second clamp member operative in an unclamped mode such that the second elongated rod can translate along its axis relative to the second clamp member and a clamped mode such that movement of second elongated rod relative to second clamp member is arrested;

first fastener connecting the first and second clamp member, the first fastener rotatable in a first direction for independently drawing together the first and second jaw portion of the second clamp member to the clamped mode such that rotation of the first fastener does not interfere with movement of first elongated rod relative to the clamp member, a second fastener connecting the first and second jaw portion of the first clamp member, the second fastener rotatable in the direction for independently drawing together the first and second jaw portion of the first clamp member.

12. The clamp assembly of an external fixation system for connecting first and second elongated members of claim 1, further comprising a second fastener connecting the first and second jaw portions of the first clamp member, the second fastener rotatable in the first direction for independently drawing together the first and second jaw portions of the first clamp member to the clamped mode such that rotation of the second fastener does not interfere with movement of the elongated rod relative to the first clamp member.

13. The clamp assembly of an external fixation system for connecting first and second elongated members of claim 12, wherein the first and second fasteners are substantially co-linear.

14. The clamp assembly of an external fixation system for connecting first and second elongated members of claim 12, wherein the second fastener is hollow and the first fastener passes through the second fastener.

15. The clamp assembly of an external fixation system for connecting first and second elongated members of claim 12, wherein the second fastener passes through an aperture provided in the first jaw portion of the first clamp member and threadably engages the second jaw portion of the second clamp member.

16. The clamp assembly of an external fixation system for connecting first and second elongated members of claim 11, wherein rotation of the first fastener in the first direction further functions to draw together the first and second clamp members and permit relative rotation therebetween.

17. The clamp assembly of an external fixation system for connecting first and second elongated members of claim 11, wherein adjacent surfaces of the first and second clamp members each include a plurality of cooperating serrations that interlock with each other to prevent relative rotation.

18. A clamp assembly for an external fixation system, the clamp assembly comprising:

a first elongated rod;

a second elongated rod;

a first clamp member receiving the first elongated rod, the first clamp member including a first fastener rotatably in a first direction to lock the first elongated member relative to the first clamp member;

a second clamp member receiving the second elongated rod; and a second fastener connecting the first and second clamp members, the second fastener rotatable in the first direction to independently lock the second elongated member relative to the second clamp member;

wherein the first and second clamp members are lockable independently through rotation of the first and second fasteners, respectively, such that rotation of the first fastener does not interfere with clamping of the second elongated rod within the second clamp member and rotation of the second fastener does not interfere with clamping of the first elongated rod within the first clamp member.

19. The clamp assembly for an external fixation system of claim 18, wherein the first and second fasteners are substantially co-linear.

20. The clamp assembly for an external fixation system of claim 18, wherein the first fastener is hollow and the second fastener passes through the first fastener.

21. The clamp assembly for an external fixation system of claim 18, wherein the second fastener passes through an aperture provided in the first jaw portion of the first clamp member and threadably engages the second jaw portion of the second clamp member.

22. The clamp assembly for an external fixation system of claim 18, wherein rotation of the first fastener in the first direction further functions to draw together the first and second clamp members and permit relative rotation therebetween.

23. The clamp assembly for an external fixation system of claim 18, wherein adjacent surfaces of the first and second clamp members each include a plurality of cooperating serrations that interlock with each other to prevent relative rotation.

24. A method of securing the relative positions of a first elongated member and a second elongated member with a clamp assembly including first and second clamp members connected by a fastener, the method comprising the steps of:

engaging the first elongated member with the first clamp member;

engaging the second elongated member with the second clamp member;

rotating the fastener to prevent relative rotation between the first and second clamp members about an axis of the fastener and to prevent relative movement between the first elongated member and the first clamp member; and moving the second elongated member relative to the second clamp member along an axis defined by the second elongated member while relative rotation between the first and second clamp members is prevented and relative movement between the first elongated member and the first clamp member is prevented.

25. The method of claim 24, wherein adjacent surfaces of the first and second clamp members each include a plurality of cooperating serrations that interlock with each other and wherein the step of rotating the fastener to prevent relative movement between the first and second clamp members includes the step of drawing together the first and second clamp members.

26. The method of claim 24, wherein the clamp assembly further includes a second fastener connecting first and second jaw portions of the second clamp member and the method further comprises the step of rotating the second fastener to arrest relative movement between the second elongated member and the second clamp member without affecting freedom of movement between the first and second clamp members and freedom of movement between the first elongated member and the first clamp member.

27. The method of claim 24, wherein the step of engaging the first elongated member with the first clamping member includes the step of resiliently displacing a cantilevered arm of the first clamping member with the first elongated member through elastic deformation of the first clamp member.

28. The method of claim 24, further comprising the step of locking the second clamp member to the second elongated member to prevent relative movement therebetween.

29. The method of claim 19, wherein the step of locking the second clamp member to the second elongated member includes the step of further rotating the fastener.

* * * * *

UNITED STATES PATENT AND TRADEMARK OFFICE
CERTIFICATE OF CORRECTION

PATENT NO. : 6,616,664 B2
DATED : September 9, 2003
INVENTOR(S) : Walulik et al.

It is certified that error appears in the above-identified patent and that said Letters Patent is hereby corrected as shown below:

Column 5,
Line 67, delete "cone" and substitute -- done -- therefor.

Column 11,
Line 3, delete "particular" and substitute -- particularly -- therefor.

Column 13,
Line 15, after "and" insert -- second --.
Line 28, after "to" insert -- the --.
Line 29, insert -- a -- before "first".
Line 38, before "direction" insert -- first --.

Column 14,
Line 11, delete "rotatably" and substitute -- rotatable -- therefor.

Column 16,
Line 10, "claim 19" should be -- claim 28 --.

Signed and Sealed this

First Day of March, 2005

JON W. DUDAS
*Director of the United States Patent and Trademark Office*